United States Patent
Debunne et al.

(10) Patent No.: US 9,468,679 B2
(45) Date of Patent: Oct. 18, 2016

(54) METHOD FOR PRODUCING SOLID FORMULATIONS COMPRISING IMMUNOGLOBULIN SINGLE VARIABLE DOMAINS

(75) Inventors: Ann Debunne, De Pinte (BE); Veronique De Brabandere, Gent (BE)

(73) Assignee: Ablynx N.V., Zwijnaarde (BE)

( * ) Notice: Subject to any disclaimer, the term of this patent is extended or adjusted under 35 U.S.C. 154(b) by 278 days.

(21) Appl. No.: 14/008,002

(22) PCT Filed: Mar. 28, 2012

(86) PCT No.: PCT/EP2012/055497
§ 371 (c)(1),
(2), (4) Date: Nov. 15, 2013

(87) PCT Pub. No.: WO2012/130872
PCT Pub. Date: Oct. 4, 2012

(65) Prior Publication Data
US 2014/0065145 A1    Mar. 6, 2014

Related U.S. Application Data

(60) Provisional application No. 61/468,341, filed on Mar. 28, 2011.

(51) Int. Cl.
*A61K 39/395* (2006.01)
*A61K 39/44* (2006.01)
*A61K 9/16* (2006.01)
*C07K 16/00* (2006.01)

(52) U.S. Cl.
CPC .............. *A61K 39/44* (2013.01); *A61K 9/1635* (2013.01); *A61K 9/1652* (2013.01); *A61K 9/1676* (2013.01); *A61K 39/39591* (2013.01); *C07K 16/00* (2013.01); *C07K 2317/22* (2013.01); *C07K 2317/569* (2013.01)

(58) Field of Classification Search
None
See application file for complete search history.

(56) References Cited

U.S. PATENT DOCUMENTS

| 6,423,517 B2 | 7/2002 | Becker et al. |
| 6,596,318 B2 | 7/2003 | Prasch et al. |
| 2005/0053666 A1 | 3/2005 | Tzannis et al. |
| 2007/0110802 A1 | 5/2007 | Jona et al. |
| 2010/0003253 A1 | 1/2010 | Laeremans et al. |

FOREIGN PATENT DOCUMENTS

| DE | 4441167 C1 | 3/1996 |
| EP | 2 036 574 A1 | 3/2009 |
| WO | WO 2005/055976 A2 | 6/2005 |
| WO | WO 2005/067898 A2 | 7/2005 |
| WO | WO 2005/123131 A2 | 12/2005 |

OTHER PUBLICATIONS

Hosny et al., Oral delivery of insulin from enteric-coated capsules containing sodium salicylate: effect on relative hypoglycemia of diabetic beagle dogs. Int J Pharm. Apr. 26, 2002;237(1-2):71-6.
Iveson et al., Nucleation, growth and breakage phenomena in agitated wet granulation processes: a review. Powder Technology. 2001;117:3-39.
Kristensen et al., Granulation: A Review on Pharmaceutical Wet-Granulation. Drug Dev Ind Pharm. 1987;13(4-5):803-872.
Lee, Spray-drying of proteins. Pharm Biotechnol. 2000;13:135-58.
Leuenberger et al., Spray freeze drying in a fluidized bed at normal and low pressure. Drying Technology. 2006;24:711-719.
Loh et al., Spray granulation for drug formulation. Expert Opin Drug Deliv. Dec. 2011;8(12):1645-61. doi:10.1517/17425247.2011.610304.
Maa et al., Spray-coating for biopharmaceutical powder formulations: beyond the conventional scale and its application. Pharm Res. Mar. 2004;21(3):515-23.
Menon et al., Identifying fluid-bed parameters affecting product variability. Int J Pharma. Aug. 1996;140(2):207-218.
Shlieout, Purified proteins as APIs in solid dosage forms? BioProcess International. European Conference & Exhibition. Apr. 7, 2011.
Sollohub et al., Spray drying technique: II. Current applications in pharmaceutical technology. J Pharm Sci. Feb. 2010;99(2):587-97. doi:10.1002/jps.21963.
Vehring, Pharmaceutical particle engineering via spray drying. Pharm Res. May 2008; 25(5):999-1022. Epub Nov. 28, 2007.

*Primary Examiner* — Yunsoo Kim
(74) *Attorney, Agent, or Firm* — Wolf, Greenfield & Sacks, P.C.

(57) ABSTRACT

Methods for preparing solid formulations of immunoglobulin single variable domains are provided. The methods are based on contacting solid carrier(s) with a liquid comprising the immunoglobulin single variable domains, e.g. by spraying the liquid onto the solid carrier(s), to cause granulation or coating of the carrier(s). During contacting the carrier is agitated, e.g. in a fluid bed, and the mixture of carrier and liquid is exposed to heat, e.g. a heated air stream, to evaporate the liquid.

21 Claims, No Drawings

SEQUENCE LISTING

```
<160> NUMBER OF SEQ ID NOS: 3

<210> SEQ ID NO 1
<211> LENGTH: 118
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Arg Phe Arg Thr Ala Ala Gln Gly Thr Asp Tyr Trp Gly Gln Gly Thr
            100                 105                 110

Gln Val Thr Val Ser Ser
        115

<210> SEQ ID NO 2
<211> LENGTH: 259
<212> TYPE: PRT
<213> ORGANISM: Artificial Sequence
<220> FEATURE:
<223> OTHER INFORMATION: Nanobody sequence

<400> SEQUENCE: 2

Asp Val Gln Leu Val Glu Ser Gly Gly Gly Leu Val Gln Pro Gly Gly
```

```
            1               5                  10                 15
Ser Leu Arg Leu Ser Cys Ala Ala Ser Gly Arg Thr Phe Ser Tyr Asn
            20                 25                 30

Pro Met Gly Trp Phe Arg Gln Ala Pro Gly Lys Gly Arg Glu Leu Val
        35                 40                 45

Ala Ala Ile Ser Arg Thr Gly Gly Ser Thr Tyr Tyr Pro Glu Ser Val
    50                 55                 60

Glu Gly Arg Phe Thr Ile Ser Arg Asp Asn Ala Lys Arg Thr Val Tyr
65                 70                 75                 80

Leu Gln Met Asn Ser Leu Arg Ala Glu Asp Thr Ala Val Tyr Tyr Cys
                85                 90                 95

Ala Ala Ala Gly Val Arg Ala Glu Gln Gly Arg Val Arg Thr Leu Pro
            100                105                110

Ser Glu Tyr Thr Phe Trp Gly Gln Gly Thr Gln Val Thr Val Ser Ser
        115                120                125

Ala Ala Ala Glu Val Gln Leu Val Glu Ser Gly Gly Gly Leu Val Gln
    130                135                140

Pro Gly Gly Ser Leu Arg Leu Ser Cys Ala Ala Ser Gly Arg Thr Phe
145                150                155                160

Ser Tyr Asn Pro Met Gly Trp Phe Arg Gln Ala Pro Gly Lys Gly Arg
                165                170                175

Glu Leu Val Ala Ala Ile Ser Arg Thr Gly Gly Ser Thr Tyr Tyr Pro
            180                185                190

Glu Ser Val Glu Gly Arg Phe Thr Ile Ser Arg Asp Asn Ala Lys Arg
        195                200                205

Thr Val Tyr Leu Gln Met Asn Ser Leu Arg Ala Glu Asp Thr Ala Val
    210                215                220

Tyr Tyr Cys Ala Ala Ala Gly Val Arg Ala Glu Gln Gly Arg Val Arg
225                230                235                240

Thr Leu Pro Ser Glu Tyr Thr Phe Trp Gly Gln Gly Thr Gln Val Thr
                245                250                255

Val Ser Ser

<210> SEQ ID NO 3
<211> LENGTH: 408
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Val Glu Ser Gly Gly Gly Leu Val Gln Ala Gly Gly
1               5                  10                 15

Ser Leu Ser Ile Ser Cys Ala Ala Ser Gly Gly Ser Leu Ser Asn Tyr
            20                 25                 30

Val Leu Gly Trp Phe Arg Gln Ala Pro Gly Lys Glu Arg Glu Phe Val
        35                 40                 45

Ala Ala Ile Asn Trp Arg Gly Asp Ile Thr Ile Gly Pro Pro Asn Val
    50                 55                 60

Glu Gly Arg Phe Thr Ile Ser Arg Asp Asn Ala Lys Asn Thr Gly Tyr
65                 70                 75                 80

Leu Gln Met Asn Ser Leu Ala Pro Asp Thr Ala Val Tyr Tyr Cys
                85                 90                 95

Gly Ala Gly Thr Pro Leu Asn Pro Gly Ala Tyr Ile Tyr Asp Trp Ser
            100                105                110
```

```
Tyr Asp Tyr Trp Gly Arg Gly Thr Gln Val Thr Val Ser Ser Gly Gly
        115                 120                 125
Gly Gly Ser Gly Gly Gly Ser Gly Gly Gly Ser Glu Val Gln
    130             135             140
Leu Val Glu Ser Gly Gly Leu Val Gln Ala Gly Gly Ser Leu Ser
145             150             155             160
Ile Ser Cys Ala Ala Ser Gly Gly Ser Leu Ser Asn Tyr Val Leu Gly
                165             170             175
Trp Phe Arg Gln Ala Pro Gly Lys Glu Arg Glu Phe Val Ala Ala Ile
            180             185             190
Asn Trp Arg Gly Asp Ile Thr Ile Gly Pro Pro Asn Val Glu Gly Arg
        195             200             205
Phe Thr Ile Ser Arg Asp Asn Ala Lys Asn Thr Gly Tyr Leu Gln Met
    210             215             220
Asn Ser Leu Ala Pro Asp Asp Thr Ala Val Tyr Tyr Cys Gly Ala Gly
225             230             235             240
Thr Pro Leu Asn Pro Gly Ala Tyr Ile Tyr Asp Trp Ser Tyr Asp Tyr
            245             250             255
Trp Gly Arg Gly Thr Gln Val Thr Val Ser Ser Gly Gly Gly Gly Ser
            260             265             270
Gly Gly Gly Gly Ser Gly Gly Gly Gly Ser Glu Val Gln Leu Val Glu
        275             280             285
Ser Gly Gly Gly Leu Val Gln Ala Gly Gly Ser Leu Ser Ile Ser Cys
    290             295             300
Ala Ala Ser Gly Gly Ser Leu Ser Asn Tyr Val Leu Gly Trp Phe Arg
305             310             315             320
Gln Ala Pro Gly Lys Glu Arg Glu Phe Val Ala Ala Ile Asn Trp Arg
            325             330             335
Gly Asp Ile Thr Ile Gly Pro Pro Asn Val Glu Gly Arg Phe Thr Ile
            340             345             350
Ser Arg Asp Asn Ala Lys Asn Thr Gly Tyr Leu Gln Met Asn Ser Leu
            355             360             365
Ala Pro Asp Asp Thr Ala Val Tyr Tyr Cys Gly Ala Gly Thr Pro Leu
        370             375             380
Asn Pro Gly Ala Tyr Ile Tyr Asp Trp Ser Tyr Asp Tyr Trp Gly Arg
385             390             395             400
Gly Thr Gln Val Thr Val Ser Ser
                405
```

METHOD FOR PRODUCING SOLID FORMULATIONS COMPRISING IMMUNOGLOBULIN SINGLE VARIABLE DOMAINS

RELATED APPLICATIONS

This application is a national stage filing under 35 U.S.C. §371 of international application PCT/EP2012/055497, filed Mar. 28, 2012, which was published under PCT Article 21(2) in English, and claims the benefit under 35 U.S.C. §119(e) of U.S. provisional application Ser. No. 61/468,341, filed Mar. 28, 2011, the disclosures of which are incorporated by reference herein in their entireties.

FIELD OF THE INVENTION

The present invention relates to methods for preparing solid formulations of immunoglobulin single variable domains. The methods are based on contacting solid carrier(s) with a liquid comprising the immunoglobulin single variable domains, e.g. by spraying the liquid onto the solid carrier(s), to cause granulation or coating of the carrier(s). During contacting the carrier is agitated, e.g. in a fluid bed, and the mixture of carrier and liquid is exposed to heat, e.g. a heated air stream, to evaporate the liquid. Thereby the solid formulation of the invention is formed.

BACKGROUND ART

Solid formulations such as powders, granules or tablets are widely used in pharmaceutical industry. They typically comprise at least one active ingredient, and may further comprise carriers and other excipients. Solid formulations are also used in other commercial applications, e.g. in the diagnostic area, such as in the manufacture of diagnostic kits. Granules can be used e.g. in capsules, sachets or processed further (e.g. pressed) to tablets. Advantages offered by solid formulations include less storage space, ease of handling, and improved stability. Moreover, tablets or capsules provide the most widely used dosage unit for applying drugs to a patient in a non-invasive manner. A long established practice of preparing solid formulations exists for small molecule active ingredients.

In the meanwhile, immunoglobulins are finding ever-increasing use as active ingredients in therapeutic or diagnostic applications. These applications rely on the antigen binding activity of immunoglobulins.

In comparison to small molecule drugs, immunoglobulins are very large and complex molecules. They carry multiple functional groups and form complex three dimensional structures. The correct folding into a tertiary structure, and, potentially, the assembly of multiple domains or subunits of such three dimensional structures into a quaternary structure are essential for antigen binding. For example, binding of an immunoglobulin variable domain to its antigen depends on the correct formation of the antigen binding site, and thus, on the correct overall folding of the molecule.

Complexity in terms of chemical composition and structure imposes severe limits on methods for preparing solid formulations that comprise biologically active immunoglobulins. The main problem associated with methods for solid formulation of immunoglobulins is protein instability, in particular chemical instability and physical instability.

Chemical instability is caused by changes in the composition of proteins through bond formation or cleavage. Examples of chemical protein instability include deamidation, racemization, hydrolysis, isomerizatin, dehydration, oxidation, beta elimination, glycation, and disulfide exchange/scrambling.

Physical instability affects protein structure. Changes in temperature, shear stress, effects caused by phase interfaces (e.g. liquid/gas), and loss of hydration effects each can result in physical instability of immunoglobulins, such as changes to higher order structure (i.e. aggregation), denaturation or unfolding, adsorption and precipitation. The biological function of macromolecules such as immunoglobulins relies on their native conformation, which is maintained by temperature-sensitive hydrogen bonds or non-covalent interactions between functional groups of the macromolecule. When an immunoglobulin is exposed to increased temperature over a critical level known as the melting temperature (Tm) or the denaturation temperature (Td) it undergoes a sharp structural transition and denatures. Typically this temperature-induced structural transition is irreversible. It is known, for example, that immunoglobulin domains are vulnerable to heat induced unfolding. This in turn leads to exposure of hydrophobic patches which interact to form irreversible aggregates.

It goes without saying that chemical and physical instability interact in compromising biological activity. The resulting loss of activity is incompatible with a pharmaceutical or diagnostic application of such solid immunoglobulin formulations.

All the above effects on physical or chemical stability are favoured by exposure to heat in a liquid state. Moreover, they are favoured by a high interface area between the liquid and gas phase.

It is widely known that proteins can withstand higher temperatures in a dry state than in a liquid state.

Thus, of particular concern for immunoglobulin stability is the combination of heat and a liquid state, in particular under additional shear stress conditions and the presence of large phase interface surfaces. Immunoglobulins that are heated in a liquid state will suffer from chemical modifications, in addition to loosing their proper structure by aggregation and denaturing.

Consequently, strategies have been deployed to avoid temperature induced denaturing. These strategies include a) shorten the time of exposure to high temperature during drying (e.g. spray-drying based on flash evaporation); b) reducing moisture: water content has a great impact on thermal denaturation of proteins being formulated or stored in a powder form. Increase of water content results in a decrease of Td and enthalpy of denaturation and increased protein mobility.

The problems encountered with macromolecular protein therapeutics such as immunoglobulins are not as pronounced in very small peptides. In particular, very small peptides differ in terms of their instability from a chemical, biological and physical point of view. Irreversible conformation changes including aggregation typically are absent in very small peptides. In other words, even if a peptide suffers from conformation changes in the course of a formulation process, it may regain a functional conformation under appropriate conditions and thus regain its activity. For example, solid formulations of insulin are known (e.g. Hosny et al., 2002; J. Pharm. 237(1-2): 71-6). This is in stark contrast to the irreversible changes of macromolecular protein therapeutics which irreversibly loose their activity, and is one reason why much effort has been put in commercializing very small peptides and small molecules instead of proteins in particulate solid dosage forms.

Therefore known methods for preparing solid immunoglobulin formulations avoid the exposure to elevated temperatures in a liquid state and under shear stress. In particular, commonly used methods for solid formulation of immunoglobulins include freeze drying (lyophilization). Freeze drying operates at very low temperatures and thus avoids immunoglobulin instability caused by exposure to heat in a liquid state. However, the solid formulations obtainable by freeze drying typically are not directly suitable for the manufacture of e.g. tablets, capsules or implants. This necessitates complicated and expensive further processing, if such solid dosage forms are to be produced. Therefore, the art attempted to modify and improve freeze drying processes (Leuenberger et al. 2006; Drying Technology 24: 711-719).

Another known method for gentle production of solid state formulations comprising proteins is spray drying, or combinations of freeze-drying and spray drying (e.g. Lee 2000; Pharm. Biotechnol. 13: 135-58; Sollohub and Cal 2010; J. Pharm. Sci. 99(2): 587-97; Vehring 2008; Pharm. Res. 25(5): 99-1022).

Spray drying is based on the principle that a liquid comprising the active agent is sprayed into a hot stream of gas, e.g. air, and vaporised. Droplet size is adjusted (e.g. 20 μm) to maximize surface area for heat transfer and the rate of water evaporation. Solids are formed as moisture quickly leaves the droplets. During this process evaporation has a cooling effect on the droplets. Because of the advantageous ratio of volume to surface area of the droplets, spray dryers can dry a product very quickly compared to other methods of drying. Thus, exposure to heat in a liquid state is reduced to a minimum, and the conversion to a solid state is almost immediate (e.g. in the range of a few seconds). Moreover, the evaporation of the droplets is not associated with shear stress for the active agent.

However, there remains a need for further methods for preparing solid formulations comprising immunoglobulin single variable domains.

The present invention is based on the unexpected finding that a solid formulation comprising, as an active agent, immunoglobulin single variable domains, in particular (camelid) VHH domains, camelized VH domains or humanized VHH domains can be produced by a method combining heat exposure in a liquid state and shear stress, without significant loss of biological activity.

SUMMARY OF THE INVENTION

The present invention provides a method of producing a solid formulation of an immunoglobulin single variable domain, wherein a solid carrier material is agitated and contacted with a liquid comprising an immunoglobulin single variable domain as an active agent and concomitantly heat is applied to evaporate the liquid. In a particular embodiment of the invention, the method can be a wet granulation process, such as a fluid bed granulation process.

The invention in one particular embodiment relates to one or more immunoglobulin single variable domains selected from a VHH immunoglobulin single variable domain, a humanized VHH immunoglobulin single variable domain or a camelized VH immunoglobulin single variable domain or any suitable fragment thereof. The invention in one particular embodiment relates to one or more monovalent immunoglobulin single variable domains and/or one or more multivalent immunoglobulin variable domains, such as one or more bivalent immunoglobulin single variable domains or one or more trivalent immunoglobulin single variable domains.

According to the invention, the solid carrier material can be one or more selected from disaccharides like lactose, maltitol, sucrose, maltose; polyols or sugar alcohols like mannitol, sorbitol, isomalt; calcium phosphate; polysaccharides such as maltodextrin, starch and starch derivatives, pregelatinised starch, inulin; cellulose; or mixtures thereof but is not limited to these particular examples. In a preferred aspect, the solid carrier material is mannitol.

The invention also encompasses the use of additional binders, such as one or more selected from starch, starch paste, partially pregelatinised starch, gelatine and cellulose derivatives such as hydroxypropylmethyl cellulose, hydroxyethyl cellulose, hydroxypropyl cellulose (HPC), polyvinyl pyrollidone (PVP), copovidone, polydextrose, carbomer or mixtures thereof. In a particular aspect, the binder is selected from hydroxypropyl cellulose and polyvinyl pyrollidone, preferably hydroxypropyl cellulose.

In one particular embodiment, the invention relates to a coating process, in particular a fluid bed coating process. The coating process may comprise solid carrier selected from powders and beads, in particular inert nonpareil heads, more in particular beads selected from one or more of microcrystalline cellulose, sucrose, or mixtures thereof.

According to some embodiments of the invention, the liquid is evaporated to a content of less than 10% (w/w), preferably less than 5%, less than 2.5% or less than 1% of the final solid formulation.

The methods of the invention include embodiments, wherein the solid carrier is agitated by one or more of mixing, stirring, shaking, by applying a gas stream, or by combinations thereof.

In exemplary embodiments of the methods of the invention, heat may be applied in the form of a heated gas stream, preferably a heated air stream, which is directed at the solid carrier material such that a fluid bed is formed.

In exemplary embodiments the methods of the invention are performed, wherein the temperature of the solid carrier material contacted with a liquid comprising an immunoglobulin single variable domain as an active agent ranges between 40° C. and 80° C., more specifically between 40° C. and 70° C., preferably between 40° C. and 60° C., more preferably between 40° C. and 55° C., wherein each of the values is understood to allow for a variation of ±2° C.

In an exemplary embodiment of the methods of the invention, the solid carrier material is contacted with the liquid comprising an active agent by spraying, in particular by spraying the liquid onto a fluid bed of the solid carrier material.

The methods of the invention may in certain embodiments have a duration of at least 15 min, for example at least 20 min, at least 30 min, at least 40 min, at least 50 min.

In the methods of the invention the liquid comprising the active agent can be selected from water or an aqueous buffer. The liquid may further comprise excipients.

Furthermore, the invention encompasses methods that comprise further steps for preparing a pharmaceutical preparation such as a capsule, tablet or implant.

The invention also encompasses methods for preparing pharmaceutical preparations which are using a solid formulation obtainable by the method according to any aspect of the invention.

The invention also relates to a solid formulation obtainable by a method as described above, such as a pharmaceutical preparation.

DETAILED DESCRIPTION OF THE INVENTION

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd.Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

Immunoglobulin Single Variable Domain

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs.

The terms "immunoglobulin single variable domains", or "single variable domain" hence do not comprise conventional immunoglobulins or their fragments which require interaction of at least two variable domains for the formation of an antigen binding site. This is also the case for embodiments of the invention which "comprise" or "contain" an immunoglobulin single variable domain. In the context of the present invention, such embodiments exclude conventional immunoglobulins or their fragments. Thus, a construct or peptide that "comprises" or "contains" an immunoglobulin single variable domain may relate to e.g. constructs comprising more than one immunoglobulin single variable domain. Alternatively, there may be further constituents other than the immunoglobulin single variable domains, e.g. auxiliary agents of different kinds, protein tags, colorants, dyes, etc. However, the terms "immunoglobulin single variable domains" or "single variable domain" do comprise fragments of conventional immunoglobulins wherein the antigen binding site is formed by a single variable domain.

The amino acid sequence and structure of an immunoglobulin sequence such as an immunoglobulin single variable domain, in particular a Nanobody, can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region" or "CDR1"; as "Complementarity Determining Region 2" or "CDR2"; and as "Complementarity Determining Region 3" or "CDR3", respectively.

Thus, generally, single variable domains will be amino acid sequences that consist of, or essentially consist of 4 framework regions (FR1 to FR4 respectively) and 3 complementarity determining regions (CDR1 to CDR3 respectively). "Essentially consist" in this context means that additional elements such as e.g. tags used for purification or labelling may be present, but such additional elements are small as compared to the immunoglobulin single variable domain per se, and do not interfere with the antigen binding activity of the immunoglobulin single variable domain.

The total number of amino acid residues in a VHH immunoglobulin single variable domain, a humanized VHH or camelized VH, or a Nanobody, respectively, can be in the region of 110-120, is preferably 112-115, and is most preferably 113. It should however be noted that parts, fragments, analogs or derivatives (as further described herein) are not particularly limited as to their length and/or size, as long as such parts, fragments, analogs or derivatives meet the further requirements outlined herein, in particular show antigen binding activity, and are also preferably suitable for the purposes described herein.

"Suitable fragments" of immunoglobulin single variable domains relate to polypeptides which contain fewer amino acids than a native immunoglobulin single variable domain, but still show antigen binding activity (which will then usually contain at least some of the amino acid residues that form at least one of the CDR's, as further described herein). Such single variable domains and fragments most preferably comprise an immunoglobulin fold or are capable for forming, under suitable conditions, an immunoglobulin fold. More specifically, immunoglobulin single variable domains and their fragments are such that they are capable of binding to the target antigen. As such, the single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

For example, the immunoglobulin single variable domains may be a domain antibody or may be a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$ sequence); other single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341 (6242): 544-6), to Holt et al. 2003 (Trends Biotechnol. 21(11): A84-490), as well as to for example WO 04/068820, WO 06/030220, WO 06/003388 and other published patent applications of Domantis Ltd. It should also be noted that, although less preferred in the context of the present invention because they are not of mammalian origin single variable domains can be derived from certain species of shark (for example, the so-called "igNAR domains", see for example WO 05/18629).

In particular, the amino acid sequence of the invention may be a Nanobody® or a suitable fragment thereof. For a further description of $V_{HH}$'s and Nanobodies, reference is made to the review article by Muyidermans 2001 (in Reviews in Molecular Biotechnology 74: 277-302); as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817WO 03/035694, WO 03/054016 and WO 03/055527 of the Viaams Instituut voor Biotechnologie (VIB); WO 03/050531 of Algonomics N.V, and Ablynx N.V.; WO 01/90190 by the National Research Council of Canada; WO 03/025020 EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular $V_{HH}$ sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 07/104,529.

Thus, in the meaning of the present invention, the term "immunoglobulin single variable domain", or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as previously described.

Thus, in preferred embodiments of the methods according to the invention the immunoglobulin single variable domain comprises one or more selected from a VHH immunoglobulin single variable domain, a humanized VHH immunoglobulin single variable domain or a camelized VH immunoglobulin single variable domain or any suitable fragment or combination thereof.

Unless indicated otherwise, the term "immunoglobulin"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

The immunoglobulin single variable domains provided by the invention are preferably in isolated form or essentially isolated form, or form part of a protein or polypeptide of the invention, which may comprise or essentially consist of one or more immunoglobulin single variable domains and which may optionally further comprise one or more further amino acid sequences (all optionally linked via one or more suitable linkers). For example, and without limitation, the one or more immunoglobulin single variable domains may be used as a binding unit in such a protein or polypeptide, which may optionally contain one or more further amino acid sequences that can serve as a binding unit (e.g. against one or more other antigens and/or targets), so as to provide a monovalent, multivalent or multispecific polypeptide of the invention, respectively, all as described herein. Such a protein or polypeptide may also be in isolated or essentially isolated form. Thus, according to the invention, immunoglobulin single variable domains comprise constructs comprising two or more antigen binding units in the form of single variable domains, as outlined above. For example, two (or more) immunoglobulin single variable domains with the same or different antigen specificity can be linked to form e.g. a bivalent, trivalent or multivalent construct. By combining immunoglobulin single variable domains of two or more specificities, bispecific, trispecific etc. constructs can be formed. For example, a polypeptide according to the invention may comprise two immunoglobulin single variable domains directed against target A, and one immunoglobulin single variable domain against target B. Such Constructs and modifications thereof, which the skilled person can readily envisage, are all encompassed by the present invention.

Generally, polypeptides that comprise or essentially consist of a single immunoglobulin single variable domain (such as a single Nanobody) will be referred to herein as "monovalent" polypeptides or as "monovalent constructs". Polypeptides that comprise or essentially consist of two or more immunoglobulin single variable domain (such as at least two Nanobodies) will be referred to herein as "multivalent" proteins or polypeptides or as "multivalent constructs". Some non-limiting examples of such multivalent constructs will become clear from the further description herein.

According to one specific, but non-limiting aspect, a polypeptide of the invention is a bivalent construct and comprises or essentially consists of two immunoglobulin single variable domains, such as two Nanobodies. According to another specific, but non-limiting aspect, a polypeptide of the invention is a trivalent construct and comprises or essentially consists of three immunoglobulin single variable domains, such as three Nanobodies.

In the above constructs, the one or more immunoglobulin single variable domains and/or Nanobodies may be directly linked to each other and/or suitably linked to each other via one or more linker sequences.

The invention includes immunoglobulin sequences of different origin, comprising mouse, rat, rabbit, donkey, human and camelid immunoglobulin sequences. The invention also includes fully human, humanized or chimeric immunoglobulin sequences. For example, the invention comprises camelid immunoglobulin sequences and humanized camelid immunoglobulin sequences, or camelized domain antibodies, e.g. camelized Dab as described by Ward et al (see for example WO 94/04678 and Davies and Riechmarin (1994; Febs Letters 339: 285-290) and (1996; Prot. Engineering 9: 531-537)). Moreover, the invention comprises fused immunoglobulin sequences, e.g. forming a multivalent and/or multispecific construct (for multivalent and multispecific polypeptides containing one or more $V_{HH}$ domains and their preparation, reference is also made to Conrath et al. 2001 (J. Biol. Chem. 276: 7346-7350), as well as to for example WO 96/34103 and WO 99/23221), and immunoglobulin sequences comprising tags or other functional moieties, e.g. toxins, labels, radiochemicals, etc., which are derivable from the immunoglobulin sequences of the present invention.

All these molecules are also referred to as "polypeptide of the invention", which is synonymous with "immunoglobulin sequences of the invention".

In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acid sequences or nucleotide sequences encoding the same, unless the context requires a more limited interpretation.

Solid Formulation of an Immunoglobulin Single Variable Domain

The present invention relates to formulations, e.g. pharmaceutical or diagnostic formulations. These formulations comprise, as active agent, immunoglobulin single variable domains. "Active agents" contribute to or are responsible for the biological effects of the formulation, e.g. therapeutic effects in a pharmaceutical composition. The biological effects may in particular be related to the antigen binding activity of the immunoglobulin single variable domains. However, it is self-evident that a solid formulation will not typically exert any biological effect unless its active agents are reverted into a suitable state, e.g. into an aqueous solution. This can be achieved prior to use, e.g. prior to administration, or as a consequence of use, e.g. after administration. For example, if a tablet or capsule comprising a solid formulation of the invention is ingested by a subject to be treated or diagnosed, the immunoglobulin single variable domains will be brought back to a liquid state e.g. within the intestinal tract.

Active agents are distinct from auxiliary compounds, carriers, excipients, etc., which do not necessarily have biological effects themselves. The invention however does not exclude the presence of further agents having biological effects in their own right.

At the same time, formulations which comprise more than one active agent, which may or may not be an immunoglobulin single variable domain, are also encompassed by the invention. Such combinations of active agents, however, always comprise at least one active agent comprising or consisting of an immunoglobulin single variable domain. The formulations are in a solid state. "Solid formulations" include powders or granules, e.g. obtainable by a granulation or coating process. Solid formulations may have the form of agglomerates, i.e. an aggregation of solid carrier particles interspersed with active agent, or the form of coated Particulate carriers, where a layer comprising the active agent is deposited on the surface of the carrier.

The term, however, also includes formulations which are obtainable by further processing. For example, if a granulate is pressed into a tablet, filled into a capsule, or formulated into an implant (which term is meant to include a depository), in particular a solid implant, than these tablets, capsules and implants also represent solid formulations according to the present invention. The formation of such solid formulations may comprise the additional use of further excipients, flavouring agents, stabilizers, etc. Thus, the solid formulations of the present invention can be adapted to standard forms of administration, such as oral, rectal, vaginal, ocular administration. In particular embodiments the solid formulations can also be adapted to administration by sublingual administration.

The present invention relates to solid formulations without limitation. "Solid formulation" means that liquid formulations are excluded. Also excluded are formulations like suspensions or slurries, which contain high amounts of liquid, such that the physical properties of the formulation are significantly influenced by the liquid. In other words, "solid formulation" as used herein relates to formulations that have a low content of liquid, i.e. they are dry or essentially dry. Typical examples of liquid content according to the invention include a content of less than 10% (w/w), preferably less than 5%, less than 2.5% or less than 1%, e.g. 0.5-1% or 0.5-5% of the solid formulation.

The immunoglobulin single variable domains comprised in the formulation must regain their activity when brought into an appropriate environment, e.g. dissolved in a liquid. Relative to the liquid formulation of the immunoglobulin single variable domains used as a starting material in the process of producing a solid state formulation, the activity of the immunoglobulin single variable domains will be e.g. at least 50%, 60% or 70%, preferably at least 80%, 90% or 95% after reconstitution of the solid formulation to a liquid state. Such a comparison will suitably employ conditions (e.g. temperature, buffer, pH), which per se do not affect the activity measurement, Activity can be determined either by a binding assay, or an assay which relies on a further biological activity (e.g. blocking a certain biological effect of the target molecule). The skilled person can readily determine suitable assays on the basis of the antigen specificity of the immunoglobulin single variable domains.

The above values of activity will preferably be stable over prolonged times of storing the solid formulation. For example, the above values of activity will be attainable after at least 1, 3 or 6 months of storage of the solid formulation at 4° C.

In the particular embodiment of fluid bed wet granulation, an activity of greater than 90%, preferably greater than 95% can be achieved, which remains at greater than 90% even after 3 months of storage at 4° C., in the embodiment of bead coating, an activity of greater than e.g. 70%, 75% or 80% can be achieved.

Apart from the stability in terms of activity of the immunoglobulin single variable domains, the solid formulations of the present invention also are characterized by integrity and stability of the immunoglobulin single variable domains in chemical and physical terms.

Physical integrity can be ascertained e.g. by size exclusion chromatography (abbreviated "SEC"). The formation of aggregates or the loss of structure e.g. by unfolding would affect the flow through properties of immunoglobulin single variable domains in this chromatographic method. The skilled person knows suitable chromatographic equipment and analysis software. Non-limiting examples include e.g. Agilent 1200 HPLC system equipped with ChemStation software (Agilent Technologies, Palo Alto, USA, Rev B); Dionex Ultimate 3000 HPLC system equipped with Chromeleon software (Dionex Corporation, Sunnyvale, Calif., USA, V6.8); or ACQUITY UPLC® H-Class Bio System (Waters, Saint-Quentin, Prance). Such systems allow for the generation and analysis of chromatograms.

Typically, a main peak comprising the immunoglobulin single variable domain may be flanked by so-called pre- or post-peaks, which represent structural variants, e.g. aggregates (higher molecular weight than the main product peak)

or fragments (lower molecular weight than the main product peak). The peaks on the chromatogram can be compared, e.g. in terms of their area under the curve. This can be achieved by standard commercial software as exemplified above. Typically, the total area under the curve of all characteristic peaks in one chromatogram is set at 100% and is also referred to as "peak area", and the distribution between different peaks of one chromatogram can be compared. For example, the main peak corresponding to immunoglobulin single variable domains can be 98%, and a pre-peak, comprising e.g. a dimeric aggregate can be 2% of the total peak area on the chromatogram. These patterns can be compared between a liquid reference and a solid formulation of the invention. Ideally, the proportion of the main peak versus the side peaks will not change, or not change significantly, by the methods of the invention.

Formulations of the present invention will only show very minor changes between the main peak and pre- or post-peaks caused by the formulation method. For example, the relative increases in pre- or post-peaks will be less than 5% for each individual peak, e.g. less than 4, 3, 2 or 1%. This means, for example, if in the reference sample a single pre-peak 1 amounts to 1% of the total area of peaks, this peak will amount to no more than 6% after preparing a solid formulation according to the methods of the present invention, and more particularly will remain at e.g. 2 or 3%, in other words, the immunoglobulin single variable domains will retain their physical integrity without significant changes. This is also reflected in that the main peak corresponding to the immunoglobulin single variable domains will be more than 90%, more than 95%, preferably more than 96, 97, or 98% of the total area under the curve even after the method of formulation of the present invention.

The above defined changes in peak pattern can also be considered as "no significant change", or "only minor changes" in the context of the present invention.

Moreover, the peak pattern will be stable at storage, and will not differ significantly (as defined above) even after e.g. 3 months storage at 4° C.

Chemical stability of the immunoglobulin single variable domains can be assessed e.g. by reversed phase chromatography (abbreviated "RPC", for suitable exemplary equipment and analysis software see above). Chemical modifications of the polypeptide will affect the retention times and thus influence the chromatogram. As in SEC, the various peaks can be analysed and compared to a reference value.

In a preferred embodiment, the formulation of the present invention will not show any significant changes in the RPC chromatogram as compared to the reference sample.

The formulation may comprise a single type of immunoglobulin single variable domain, or a mixture of two or more types of immunoglobulin single variable domains. In this context "type" means e.g. a particular immunoglobulin single variable domain sequence having a given antigen specificity, or a construct comprising two or more such immunoglobulin single variable domains, etc.

Typical examples of solid formulations, in particular granulate and/or coated beads will comprise, on a weight/weight basis, less than e.g. 50%, 40%, 30% or, preferably, less than 25% of active ingredient. The content of active ingredient relative to total weight sometimes also is referred to as "loading" or "load" of the active ingredient. Typical examples are less than 20%, less than 15%, less than 10%, and more specifically in the range of 0.1 to 10%. Specific examples of loads obtainable by a wet granulation process, e.g. a fluid bed wet granulation process, are 3, 4, 5, 6, 7, 8 or 9% loading. Specific non limiting examples of loads obtainable by a coating process, e.g. a fluid bed coating process, are 3, 4, 5, 6, 7, 8 or 9% loading.

Oftentimes a high loading is advantageous, as it results in a high specific activity of the formulation, i.e. the activity in terms of antigen binding and/or other biological effects per weight of formulation. A high specific activity advantageously leads to smaller dosage units, e.g. a smaller capsule, tablet or implant. However, in solid dosage forms, which can be applied to a patient e.g. orally, rectally, or vaginally the loading is oftentimes not critical, because even relatively large capsules, tablets or implants can be used in order to achieve the desired dosage in a patient.

Where granulate and/or coated beads are processed further, the % loading of the final dosage unit form e.g. to tablet, capsule or implant, may be lower, depending on the amount of further agents (e.g. further auxiliary agents and/or further active agents) that are added.

Constituents of Solid Formulations

Solid formulations of the invention, e.g. granulates consist of a mixture of ingredients, at least an excipient and an active agent. As used herein, the term "excipient" refers to pharmaceutically acceptable ingredients that are commonly used in the pharmaceutical technology for preparing granulate and/or solid oral dosage formulations. Examples of categories of excipients include, but are not limited to, binders, disintegrants, lubricants, glidants, stabilizers, fillers and diluents. The skilled person can readily select one or mare of the aforementioned excipients in view of the particular desired properties of the granulate and/or solid oral dosage form. The amount of each excipient used may vary within ranges conventional in the art. To the extent the skilled person requires any additional guidance we refer to the experimental section of this specification as well as general textbooks on techniques and excipients used to formulate oral dosage forms, such as The Handbook of Pharmaceutical Excipients 2003 (4th edition, Rowe et al., Eds., American Pharmaceuticals Association); and Remington: the Science and Practice of Pharmacy 2000 (20th edition, Gennaro, Ed., Lippincott Williams & Wilkins).

Of particular interest in a granulation or coating process is the solid carrier (i.e. a solid compound which is put in contact with the liquid comprising the immunoglobulin single variable domain), which is described in more detail below.

Solid Carrier Material

According to the invention the solid immunoglobulin single variable domain formulation will comprise a solid carrier material. The carrier is in the form of solid particles, which may have regular or irregular shapes, e.g. powders, crystals, or beads. The carrier material may be a single chemical compound, such as e.g. mannitol, or may be a mixture of two or more compounds. It is also envisioned that the carrier comprises further excipients as defined above. The carrier will typically be a powder or beads. Conventional carrier materials known from solid formulations e.g. in the field of pharmaceutical preparations can be used. Specifically, carrier materials will be used which do not negatively affect antigen binding by the immunoglobulin single variable domains. The skilled person can readily ascertain by routine functional tests whether a given carrier material or mixture of materials is compatible with the immunoglobulin single variable domains that are the active ingredient of the formulation.

Acceptable solid carrier materials, which are compatible with the method of the invention, e.g. a wet granulation process, more specifically a fluid bed granulation process or a high shear mixer granulation process, in particular a fluid bed granulation process, are generally known.

Specific examples of such solid carrier materials include, but are not limited to one or more selected from disaccharides like lactose, maltitol, sucrose, maltose; polyols or sugar alcohols like mannitol, sorbitol, isomalt; calcium phosphate; polysaccharides such as maltodextrin, starch and starch derivatives, pregelatinised starch inulin; cellulose; or mixtures thereof. In a preferred aspect, the solid carrier used in the wet granulation process is mannitol.

Solid carriers which are compatible with a coating process are also known to the skilled person. For example, they can be selected from powders and beads, in particular inert nonpareil beads, more in particular beads selected from one or more of microcrystalline cellulose, sucrose, or mixtures thereof.

Preferably, any carrier material will be pharmaceutically acceptable. For diagnostic applications the skilled person also knows suitable carrier materials, and oftentimes pharmaceutically acceptable carriers can be employed.

Binder

In certain embodiments the methods of the invention also comprise the use of an additional binder. Typically, binders swell or start dissolving when in contact with water, forming a gel-like consistency. Widely used binders include, but are not limited to one or more selected from starch, starch paste, partially pregelatinised starch, aqueous preparations of cornstarch, gelatine and cellulose derivatives such as methyl cellulose hydroxypropylmethyl cellulose, hydroxyethyl cellulose, hydroxypropyl cellulose, polyvinyl pyrollidone (povidone), copovidone, polydextrose, carbomer, natural gums such as acacia, or mixtures thereof. In particular, such binders are used in wet granulation formulations. (See, Remington's Pharmaceutical Sciences, 18.sup.th ed., Mack Publishing Company: Easton, Pa., 1635-1636 (1990)). In a preferred aspect, the binder used in the wet granulation process is hydroxypropyl cellulose.

Binders can typically be added to a final contribution by weight of 1-15%, more specifically 2-10%, e.g. 2-8% of the final formulation.

Further Excipients

The solid formulations of the present invention may further comprise excipients widely used in solid formulations, e.g. pharmaceutical solid formulations. Examples include fillers, flavouring agents, colorants, disintegrants or lubricants.

The disintegrant may be e.g. one of several modified starches or modified cellulose polymers, including croscarmellose sodium such as croscarmellose sodium NF Type A.

Lubricants may include magnesium stearate, calcium stearate, stearic acid, surface active agents such as sodium lauryl sulfate, propylene glycol, sodium dodecane sultanate, sodium oleate sultanate, and sodium laurate mixed with stearates and talc, sodium stearyl fumerate, and other known lubricants.

Also known and widely used in the production of solid formulations are barrier materials. Such substances can be applied e.g. as an additional layer onto a coated bead, or a granule. Barrier materials are used e.g. to produce a pH dependent release formulation, or a retarded release formulation. The skilled person can choose adequate barrier materials that are commonly known for performing the present invention.

As with all other substances for use in the methods of the present invention the skilled person will choose such agents which do not interfere with the biological activity of the active agent, and will not have a negative effect on the process of producing a solid formulation.

Salt Concentration

In any aspect of the invention is it advantageous that the total salt concentration of the liquid comprising the active agent is less than 15% (w/w), preferably less than 10%, e.g. less than 9%, 8%, 7%, 6% or 5%, wherein each value is optionally understood as comprising a range±20%, i.e. a value of 10% (w/w) is understood to relate to a range between 8 and 12%. Salts may be derived from a buffer, excipient, lubricant or any other compound used in the methods of the present invention. When e.g. a buffer and an excipient comprising salt are used, the above concentration relates to the combination of all salts.

It is also desirable that the concentration of total salts in the liquid comprising an immunoglobulin single variable domain used in the context of the present invention, e.g. buffer concentration, is relatively low, e.g. less than 30 mM, less than 20 mM, and preferably less than 10 mM, e.g. 9, 8, 7, 6, or 5 mM, wherein each value is optionally understood to encompass a range of ±20%, e.g. a value of 10 mM is understood to encompass a range of 8 to 12 RIM.

The Methods of the Invention

Granulation or coating processes are amongst the most widely used processes in preparation of solid pharmaceutical or diagnostic formulations. These solid formulations allow physical manipulation of the drugs, the manufacture of dosage forms such as tablets or capsules, and provide stable powders for storage. For example, granules or coated beads can be filled into capsules, and thus directly be used for the manufacture of this dosage form. Granules, moreover, are a widely used starting material for the manufacture of tablets, which are formed by pressing the granules into tablet form. Again, therefore, granules serve as starting material which can be converted into tablets without complicated and expensive further processing steps. In all these applications, the physical characteristics of the e.g. granules or coated beads are instrumental for the manufacturing processes of e.g. pharmaceutical preparations. The solid formulations must show suitable flow properties, be sufficiently stable to withstand the physical stress encountered during industrial manufacturing processes, and avoid the formation of dust. Importantly, established industrial processes for wet granulation or coating allow the skilled person to control the parameters of the solid formulations, such as e.g. granule size, flow characteristics, loading, etc.

Unfortunately, processes used for granulation or coating of small molecule drugs are disadvantageous for immunoglobulins. Wet granulation and coating processes require the presence of a liquid, which in turn has to be evaporated off to obtain a dry solid formulation. This requires the application of heat. The carrier/liquid mixture is physically agitated to prevent clumping and provide an even mixture of the components. This combination of process features leads to an extremely stressful environment for macromolecules such as immunoglobulins. This environment favors all aspects that are detrimental to biological activity of immunoglobulins, i.e. chemical stress (promoted by the exposure to heat, large surface interfaces, high exposure to e.g. oxygen derived from air, and prolonged process times), and various physical stresses in particular intensive shear stress by physical agitation of the mixture of solid carrier and liquid, as well as physical stress induced by phase interfaces between liquid and gas, combined with oftentimes high velocities of particles and a high frequency of collisions between particles and between particles and vessel walls in a reaction container.

It has now surprisingly been found that immunoglobulin single variable domains, like VHH, camelized VH or humanized VHH domains, can withstand standard process conditions in the production of solid formulations encountered in wet granulation or coating processes. In particular, these molecules can withstand exposure to a combination of heat in a liquid state, large gas/liquid interfaces and shear stress. Thus, surprisingly, solid formulations comprising immunoglobulin single variable domains can be prepared by using standard equipment and commonly used process parameters. The formulations nevertheless retain biological activity as well as physical and chemical integrity and share all further advantages, as further explained above.

a) Wet Granulation

Standard methods that combine wet heat and agitation of carrier materials are widely used in the production of pharmaceutical or diagnostic formulations. Specific examples include wet granulation processes, such as a fluid bed granulation processes. Pharmaceutical granulation processes are used for the production of tablets, capsules and spherical granules.

"Granulation process" means any process whereby small particles are gathered into larger permanent masses in which the original particles can still be identified. This process is also described as "agglomeration by agitation": a particulate feed, e.g. a solid carrier material is introduced to a process vessel and is agglomerated either batch-wise or continuously to form granulated product. The feed is agitated in the process vessel to cause granulation. (Perry's Chemical Engineer's Handbook, 7th edition 1997).

In wet granulation, the particulate feed is contacted with a liquid, e.g. by spraying the liquid into the process vessel. Typically the liquid will be sprayed onto the particulate feed. Apparatuses are widely known which may spray from the bottom, the top, or any other suitable orientation. The liquid acts as a binder to agglomerate the solid particulate feed. The amount of liquid has to be properly controlled, as overwetting will cause the granules to be too hard and underwetting will cause them to be too soft and friable. Thus, the amount of liquid and the rate of addition will influence the granulation process, as is widely known.

Thus, a wet granulation process will comprise at least the steps of contacting the particulate feed (the solid carrier) with a liquid comprising the immunoglobulin single variable domains and applying heat to evaporate the liquid. However, the process may optionally also comprise further steps, e.g. a pre-heating phase to bring the particulate feed to an appropriate temperature. Moreover, the contacting of the particulate feed with the liquid can be continuous or discontinuous, and may extend over the entire process, or only a part of the process. For example, the particulate feed will be contacted with the liquid for a predefined period of time, and thus a predefined amount of active agent will be contacted with the particulate feed in an equally predefined amount. Then, a separate phase of drying may ensue, wherein no additional liquid is added to the reaction vessel. Nevertheless, application of heat continues until a desired residual content of liquid is achieved. The drying phase may not be necessary, e.g. in case the liquid content is continuously kept below the desired level by adjusting the process parameters appropriately.

Process parameters that can be readily adjusted by the skilled person include the rate of particulate feed, the rate of adding the liquid, the form and intensity of applying heat, e.g. the volume and temperature of a heated gas streamed through the reaction vessel, the intensity and form of physical agitation, e.g. mixing or fluidizing by use of a gas stream, and the overall duration of the process. The skilled person can derive guidance on suitable process parameters from his common knowledge in wet granulation processes, and will find additional guidance in the experimental section of this description.

The feed comprises at least the solid carrier material, and may typically comprise a mixture of solid ingredients which may include binders, diluents, flow aids, surfactants, wetting agents, lubricants and fillers.

In the context of the present invention, wet granulation involves adding a liquid comprising the immunoglobulin single variable domains as active agent. The invention also encompasses methods wherein the liquid comprises further agents, e.g. binders such as polymeric binders.

The binders can be either predissolved in the liquid that comprises the immunoglobulin single variable domains. Alternatively, the binders can be included in the particular feed, e.g. by preblending with the other components of the particulate feed. The binders will then achieve the desired effect upon contacting with the liquid containing the active agent.

According to the invention, the solid carrier material and the liquid comprising the immunoglobulin single variable domains are contacted under agitation. The form of agitation is not limited, and includes one or more of mixing, stirring, shaking, applying a gas stream, or combinations thereof. Such agitation can be applied by using a fluid bed apparatus, pan, drum and mixer granulators. Preferably, agitation is continuous.

In principle the invention also encompasses low shear or, high shear granulation processes. Low shear granulation processes use very simple mixing equipment, and can take a considerable time to achieve a uniformly mixed state. High shear wet granulation processes use equipment that mixes the particulate solid feed and liquid at a very fast rate, and thus speeds up the manufacturing process. However, the amount of liquid that can be mixed with solid carriers in low or high shear granulation processes, without causing the solid carriers to dissolve or disintegrate, typically is limited. Immunoglobulin single variable domains are added to the solid carrier in a liquid state. The maximum concentration of immunoglobulin single variable domains in liquids is limited. The limitation of total liquid volume that can be added per unit carrier, together with the limitation in maximum concentration of immunoglobulin single variable domains results in a limitation in the load of active agent that is achievable in the final granulate by such wet granulation processes. For important pharmaceutical applications the use of such processes is therefore severely limited, insofar as the required loads cannot be achieved.

Another preferable standard method of producing solid formulations of small molecule drugs involves the use of fluidized bed apparatus for granulating and/or coating carrier particles. As compared to the above mentioned wet granulation processes, the active agent can be added, e.g. sprayed onto a carrier material continuously, whilst at the same time liquid is continuously evaporated by exposure to heat. By balancing liquid input and evaporation, disintegration of the carrier material by excess liquid is avoided. The continuous addition of active agent allows control over the load of the final solid formulation (granulate or coated bead) by adjusting the process time. The longer the active agent is applied, the higher the loads in the final solid formulation.

This method has been applied to very small peptides, such as insulin (Hosny et al. 2002; int. J. Pharm. 237(1-2): 71-6). However, in a fluidized bed granulation or coating process, the active agent is exposed to heat in a liquid state over prolonged periods of time, e.g. 30-90 min. Moreover, the continuous agitation of the carrier particles leads to intensive shear stress in the fluidized bed, as well as very large interface areas between liquid and gas phase. This prolonged exposure to heat in a liquid state under shear stress conditions has previously been considered unsuitable for producing solid state immunoglobulin formulations. It was expected to lead to loss of biological activity due to chemical and physical instability.

Thus, in a further preferred embodiment of the invention, the wet granulation method is a fluid bed granulation process. Fluid bed granulation is a wet granulation process, wherein the steps of pre-heating, granulation and drying can be performed in one process vessel.

"Fluid bed" and "fluidized bed" are used synonymously. These terms describe a state wherein particulate solid matter is agitated to behave like a liquid. It can be achieved e.g. by a gas stream, which suspends the particulate solid matter. The gas stream is also referred to as "fluidization medium".

In fluidized beds, there is good thermal transport inside the fluidized bed and good heat transfer between the bed and its container. Fluidized beds promote high levels of contact between gases and solids. They are characterized by a very high interface area between fluidization medium and solid per unit bed volume, a high relative velocity between the fluidization medium and the dispersed solid phase, a high level of intermixing of the particulate phase, and frequent particle-particle and particle-wall collisions.

Thus, in this embodiment of the invention, granules are produced e.g. in a single piece of equipment by spraying a solution onto a fluidised bed of solid carrier, e.g. a powder. In the fluid bed granulation process the particles are suspended in the air stream, which may be heated to a temperature suitable for evaporating the liquid, and the atomised liquid is sprayed on it.

It is also noted that the present invention is distinct from spray-freeze drying. In such a process, the protein drug is dissolved. The solution is nebulized in to a cryogenic medium (e.g. liquid nitrogen), which generates a dispersion of shock-frozen droplets. The dispersion is then dried in a lyophilizer. Thus, in embodiments of the invention, processes based on spray-freeze drying in a fluidized bed are excluded, not the least as they operate at very low temperatures and do not utilize the application of heat.

b) Coating Processes

Apart from wet granulation processes, which rely on particle agglomeration under the influence of a liquid comprising the immunoglobulin single variable domains, the present invention also encompasses coating processes.

A particulate solid carrier is contacted with a liquid, comprising immunoglobulin single variable domains to form an outer layer, or coat, around the particulate solid carrier. The skilled person can readily select suitable carriers and, if required, further excipients suitable for a coating process. Moreover, the skilled person knows standard equipment used for coating processes. Process parameters are equally known to the skilled person from standard coating processes, and further guidance can be found in the experimental section of the description.

The invention can be performed using commonly known solid carriers that are widely used in coating processes. Typically particulate solid carriers are selected from powders and beads. They can in particular be inert nonpareil beads, more in particular beads selected from one or more of microcrystalline cellulose, sucrose, or mixtures thereof.

In a preferred embodiment of the invention, the coating process is a fluid bed coating process. A fluid bed is formed as described above, and the liquid comprising the active agent is applied, e.g. sprayed, onto the fluid bed such that the particulate solid carrier is coated. Again, spraying direction may vary depending on the equipment used, and parameters can readily be adapted by the skilled person.

c) Common Parameters

The present invention combines the active agent in a liquid state with heat and agitation. In general, process parameters commonly used in wet granulation or coating processes can be used, provided they do not lead to inactivation of the immunoglobulin single variable domains. The skilled person is well acquainted with process parameters such as the feed rate of solid particulate carriers, the spray rate of the liquid comprising immunoglobulin single variable domains, the necessary intensity of agitation, and the level of heat exposure required for evaporating the liquid. Further guidance can be derived from the experimental section.

Heating has the effect of evaporating the liquid, such that a solid formulation comprising immunoglobulin single variable domains is formed. Heat can be applied by any means available to the skilled person, e.g. by heating the reaction vessel, by applying radiation such as microwaves, or by applying a heated gas stream. In a preferred embodiment, the mixture of particulate solid carrier and liquid comprising immunoglobulin single variable domains is contacted with a heated gas stream, e.g. heated air, to evaporate the liquid.

As described above, in those embodiments of the invention comprising a fluid bed, a gas stream is typically applied for generating the fluid bed. In these instances the gas stream can also be used to apply heat. This does not exclude additional ways to apply heat, e.g. by additional radiation, heating of the vessel walls or additional gas streams that are not involved in forming the fluid bed. In one exemplary embodiment, a fluid bed is formed by a gas stream that is directed in an appropriate way into the reaction vessel. The vessel walls as well as the gas stream are heated.

The gas that is used to form the gas stream, to form the fluid bed and/or apply heat is not limited. The skilled person knows many alternative gases that are compatible with the materials and active agents used in the process, including inert gases such as nitrogen or nobel gases, and air. In one preferred embodiment the gas is air.

The methods of the invention can be used over a wide temperature range, however, they have in common that they are performed at an elevated temperature, i.e. heat is applied. Temperatures above 30° C., more in particular above 35°±2° C. e.g. 38, 39 or 40° C. can be considered as heat. More specifically, for example, temperatures of the solid carrier material contacted with a liquid comprising an immunoglobulin single variable domain as an active agent, i.e. product temperatures range between 40° C. and 80° C., e.g. 50° C., 60° C., 70° C., more specifically between 40° C. and 70° C., preferably between 40° C. and 60° C., more preferably between 40° C. and 55° C., e.g. between 45 and 55° C., wherein each of the above values is understood to allow for a variation of ±2° C. In one embodiment the product temperature is higher than 50° C. (irrespective of moisture content), e.g. higher than 51, 52, 53 or 54° C., and may be in a range with an upper limit as defined above.

Specifically, these temperature values relate to product temperatures which will generally be lower than the temperature of e.g. a heated gas stream applied to the mixture. The temperature of the heated gas stream is also called "inlet temperature", distinct from the 'product temperature', and the "outlet temperature". The outlet temperature refers to the temperature of the gas leaving the reaction vessel. Product temperature typically is lower than the inlet temperature, e.g. due to the cooling effect of evaporation of the liquid. In particular embodiments, the inlet temperature will be 5-30° C. higher than the product temperature as specified above, e.g. 5, 10, 15, 20, 25 or 30° C. higher, wherein each value optionally relates to a range±2° C. For example, inlet temperature may be higher than 50, 55, 60, 65, 70 or 75° C.

It has surprisingly been found that immunoglobulin single variable domains can withstand high temperatures during the processes of the invention, despite being in liquid state. Previous reports related to proteins that are not immunoglobulin single variable domains have instructed the skilled person not to use product temperatures exceeding 35° C. (as exemplified in U.S. Pat. No. 6,596,318). Nevertheless, particularly gentle processes of the invention advantageously use the lowest temperatures compatible with adequate process times. The lower the temperature, the longer the evaporation of the liquid will take. This in turn may increase the level of physical and chemical stress of the process, e.g. the duration of exposure to shear stress will increase.

The skilled person can derive general guidance on suitable product temperatures from the melting temperature Tm of the immunoglobulin single variable domains and will preferably work at product temperatures that do not exceed Tm, e.g. are 1 to 5 or 1 to 10° C. below Tm, e.g. 1, 2, 3, 4 or 5° C. below Tm. However, alternatively the invention also contemplates embodiments wherein product temperatures exceed Tm, e.g. by e.g. 1, 2, 3, 4 or 5° C.

The present invention in particular relates to processes performed at atmospheric pressure, i.e. without reducing the pressure within the reaction vessel to further the evaporation of the liquid, as is described e.g. in DE 4441167.

It has surprisingly been found that the immunoglobulin single variable domains can withstand the combination of heat in a liquid state, high shear caused by agitation and the concomitant large interface areas between liquid and gas phase for prolonged periods of time. In other words, it is not required to flash-evaporate the liquid comprising immunoglobulin single variable domains. Thus, in any of the methods of the present invention the solid carrier material is agitated and contacted with a liquid comprising an immunoglobulin single variable domain and concomitantly heat is applied to evaporate the liquid for e.g. at least 15 min, for example at least 20 min, at least 30 min, at least 40 min, at least 50 min. This time-span describes the time between beginning to apply the liquid to the solid carrier material under the influence of heat, until sufficient liquid is evaporated that heat no longer has to be applied. Process time will typically be governed by the time required to reduce the liquid content in the formulation to an acceptable level, as defined above. This time will also depend on batch size, which determines the time needed for granulation. Hence, this time span may comprise a phase wherein liquid comprising the immunoglobulin single variable domains is applied, and a time span wherein this application is stopped, but exposure to heat is continued until a desired level of liquid is achieved. Liquid content of solid formulations is typically as defined above, i.e. the formulations are dry or essentially dry.

The liquid comprising the immunoglobulin single variable domains is not limited, provided it does not compromise activity of the immunoglobulin single variable domains. Suitable examples include water and standard buffers. Water, in particular demineralised water, is preferable, as it does not lead to additional particulate matter, such as salt crystals, when evaporated. As detailed above, the salt concentration of the liquid is preferably e.g. lower than 10% w/w, and/or lower than 10 mM. In embodiments of the invention the use of a "protein matrix" which is an admixture of one or more proteins and a salt at a high concentration, e.g. a salt concentration between 63.7 to 85.3% based on dry solids is excluded. In embodiments of the invention a protein matrix (i.e. a protein/salt mixture) which contributes to about 20-80% of the final granule weight is excluded.

Specifically, the invention relates to methods which do not use a liquid, comprising immunoglobulin single variable domains as a suspension of aggregated protein. Certain enzymes are known to withstand aggregation and can be formulated in very high salt concentrations, e.g. exceeding 60% of total dry weight in salt (U.S. Pat. No. 6,423,517). In contrast, activity of immunoglobulin single variable domains is compromised by aggregation or high salt concentrations. Moreover, aggregates and/or high salt concentrations are unacceptable for pharmaceutical preparations.

The methods according to any aspect of the present invention may also comprise further steps commonly employed in the production of solid formulations, e.g. solid pharmaceutical formulations. For example, the processes of the present invention can further comprise one or more steps of manufacturing a tablet, capsule or implant. The invention also relates to the production of pharmaceutical preparations comprising the solid formulation according to the present invention. The pharmaceutical formulation is not limited, and is typically a tablet, capsule or implant, i.e. a solid pharmaceutical formulation.

In view of the above it is one of the advantages of the present invention that solid formulations comprising immunoglobulin single variable domains can be prepared using standard equipment, standard ingredients and standard process parameters widely used e.g. in the pharmaceutical field. The wealth of know-how and infrastructure available for the manufacture of solid formulations can thus also be applied to the formulation of immunoglobulin single variable domains, which was not possible prior to the present invention.

The Formulations of the Present Invention

The present invention also relates to the solid formulations, per se. It has not previously been considered possible to prepare solid formulations obtainable by the methods of the present invention. For example, solid formulations obtainable by wet granulation processes are physically and chemically distinct from formulations obtainable by spray drying or lyophilisation. The same applies to pharmaceutical preparations which comprise the solid formulations obtainable by the methods of the present invention.

Thus, the present invention makes the manifold advantages of solid formulations available for immunoglobulin single variable domains as a class of active agents. These advantages include restricted mobility of immunoglobulin single variable domains and improved stability. However, the production process per se also imparts advantageous properties, such as control of particle size, loading and wide array of properties of the solid formulations, depending on the substances, such as excipients, used for their production. For example, the present invention can be used to prepare controlled release formulations or taste masking.

Granulation inter alia has the effect of improving powder flow properties and reducing fine dust through size enlargement and densification thus improving capsule filling and tabletting operations. Moreover, an active agent is physically adhered to the carrier material, such that carrier and active agent can be manipulated together. This prevents that various components unmix, and also prevents mechanical and physical problems that can be associated with e.g. a sticky protein precipitate as obtained by lyophilisation or spray drying. These advantages are shared by coating processes.

Also, fluidized bed apparatuses offer advantages such as uniform particle mixing, uniform temperature gradients, and flexibility to operate in batch and continuous production process. Additionally, fluidized bed apparatus provides an option to combine various formulation steps such as drying, granulating and coating in a single step.

Conversely, known methods or formulations do not provide these advantages. For example, freeze-drying (lyophilization) results in a "cake" rather than granules or beads. The cake does not show the flowing properties of granules or coated beads. The solid formulation obtainable by lyophilization is for these reasons not suitable for the preparation of tablets or capsules by standard industrial processes. Complex further operations (such as milling) are required, which increase the costs for the overall process, and may in addition be detrimental for the immunoglobulin single variable domains. As concerns spray drying process parameters are far more difficult to control in order to obtain suitable granules.

Apart from these advantages, solid formulations may also facilitate new routes of delivery. For example, WO 2005/067898 describes inhalation as a new route of delivery. Needle-free injections are also being used a route of delivery (see e.g. WO 2011/098518). WO 2004/041867 describes, amongst others, oral delivery of immunoglobulin single variable domains.

EXAMPLES

In the following, the present invention is described in more detail by providing specific exemplary embodiments. The scope of the invention however is not limited to these examples, and encompasses variations as described in the general part of the description as well as such that the skilled person can readily envisage on the basis of his common general knowledge.

1 Example 1

Fluid Bed Granulation 1.1 Materials and Methods
1.1.1 Immunoglobulin Single Variable Domain As a specific example of an immunoglobulin single variable domain, the Nanobody having the following sequence was used:

(SEQ ID NO: 1)
EVQLVESGGGLVQAGGSLRLSCAASGITFSINTMGWYRQAPGKQRELVALISSIGDTYYADSVKGRFTISRDNAKNT

VYLWMNSLKPEDTAVYYCKRFRTAAQGTDYWGQGTQVTVSS 1.1.2 Wet Granulation Process

A top-spray fluid-bed granulation process was applied using a 4M8-Trix fluid bed with a small upper diameter equipped with a 1 L insert.

Initial batch size was 50 Mannitol with a particle size of approximately 25 μm was used (Pearlitol 300 DC). The Nanobody solution was used as the granulation liquid. Specifically, a solution of Nanobody 5F7 (see WO 09/068, 625, SEQ ID No. 2112) at a concentration of 29.3 mg/ml in water was used as granulation liquid.

A 7.1% (w/w) Nanobody load was targeted. The solution was fed to a two-fluid nozzle (diameter 0.2 mm) by means of a peristaltic pump.

The spray rate and the inlet air volume were slightly increased during the process. At the end of the granulation process the granulated material was cooled to room temperature and transferred to an amber glass vial. The vial was stored at 5° C. The process yield was calculated as the amount of granulate collected in the reservoir divided by the theoretical amount of solids used in the formulation.

Process parameters are listed in Table 1. The composition of the granulate is shown in Table 2.

TABLE 1

Conditions of the fluid bed granulation process

| Process parameter | Target value |
|---|---|
| Inlet air volume (m3/h) | 0.11-0.55 |
| Inlet air temperature (° C.) | 50-65 |
| Outlet air temperature (° C.) | 36-43 |
| Product temperature (° C.) | 42-55 |
| Spray rate (ml/min) | 3-7 |
| Spray air pressure (bar) | 1 |
| Spray air flow (l/min) | 4 |
| Process time (s) | 2954 |

TABLE 2

Composition of the granulate (calculated)

| Material | Quantity (g/batch) |
|---|---|
| Nanobody 5F7 solution (solid) | 3.821 |
| Water Nanobody 5F7 solution* | 130.259 |
| Mannitol | 50.00 |

*Does not appear in the final product 1.1.3 Analytical Methods
Sample Preparation Approximately 30 mg of the Nanobody 5F7/mannitol granulate was weighed on an analytical balance and solubilized in approximately 200 μl MilliQ, water, in order to have a theoretical concentration of 5F7 in solution of about 10 mg/ml. The sample was vortexed until complete dissolution was obtained.

Content Measurements

To determine the concentration of Nanobody 5F7 in solution, OD280 and OD320 were measured. Blank setting and dilution of the samples were performed in MilliQ water (1/20). Dilutions were prepared in triplicate.

Purity Assay (Physical Integrity) of the Nanobodies by Size Exclusion High Performance Liquid Chromatography (SE-HPLC)

For the SE-HPLC assay a pre-packed silica gel TSK gel G2000SW$_{XL}$ column (Tosoh Bioscience) equipped with a guard column pre-column filter was used. The mobile phase was composed of 0.3 M arginine, 3.25 mM Na2HPO4.7H2O, 6.75 mM NaH2PO4.H2O and 0.005% NaN3 at pH6. UV detection was performed at 280 nm. The relative amount of protein purity was expressed as area %, and was calculated by dividing the peak area by the total integrated area.

Samples were diluted to 1 mg/ml in MilliQ water before injection on the SEC column and 10 (theoretically corresponding to 10 μg) was injected.

Purity Assay (Chemical Integrity) and Quantification of the Nanobodies by Reversed Phase High Performance Liquid Chromatography (RP-HPLC, or RPC)

In the RP-HPLC assay a Zorbax 300SB-C3 column (Agilent Technologies, Palo Alto, US) was used. The amount of the protein was determined by measuring the light absorbance of the components eluting from the RR-HPLC column and comparison with a reference sample. The identity of the Nanobodies was confirmed by comparing the relative elution time from the RP-HPLC column. The relative amount of protein purity was expressed as area %, and was calculated by dividing the peak area by the total (main peak+impurities) integrated area.

Samples were diluted to 1 mg/ml in MilliQ water before injection on the RPC column and 10 μl (theoretically corresponding to 10 μg) was injected.

Functionality Testing of 5F7 Via Surface Plasmon Resonance (Biacore)

The functionality of 5F7 formulated material was determined by a functionality assay on rhErbB2Fc (Her2; R&D Systems, Minneapolis, Minn.) to determine the percentage activity in the formulation compared to a reference 5F7 sample as previously described (see e.g. Example 10 of WO 09/068,625).

Briefly, a Biacore 3000 was used. rhErbB2Fc, (Her2) was immobilized on a chip (CMS). The chip was first preconditioned by 5 injections of 5 nM 5F7. Next the samples were diluted in triplicate (independent dilutions) to 5 nM and analyzed on the chip.

Evaluation was done using BIAevaluation software. Slopes were determined using the 'General fit' method and the linear fit model. To determine the initial binding rate (IBR) the slope from the linear regression line between 5 s and 30 s was selected. From this slope the functionality was calculated as the ratio of the slope of the sample versus the slope of the reference material.

Water Content Determination Via Karl Fischer Titration

Water content was determined by means of a Karl Fischer Titrator V30 (Mettler Toledo, US). Powder was weighed and transferred to the titration vessel, containing a Hydranal® Methanol dry (Sigma Aldrich) and stirred for 300 seconds. Titration was performed with Hydranal® Composite 2 (Sigma Aldrich).

Water Content Determination Via Loss on Drying (LOD)

Total residual solvent content was determined with a halogen Moisture Analyser HR83P (Mettler Toledo, USA). Approximately 1 g of sample was placed in an aluminum sample pan. The sample was dried for 15 minutes at a constant temperature of 105° C. Sample weight was monitored and weight loss expressed in % was recorded with 1 min interval, Determination of Bulk and Tapped Density A volumeter (J. Engelsmann AG, Ludwigshafen, Germany) was used. Approximately 40 g of the granulate was gently added to a 100 ml measuring cylinder. The volume was recorded after 0, 10 and 500 taps.

1.2 Results and Discussion

Fluid bed granulation of a Nanobody with mannitol as a carrier resulted in free-flowing powder with a Nanobody load of 4.7%. Functionality as well as physical and chemical integrity were retained after granulation. Material was stable after storage for 3 months at 4° C.

These conclusions are further supported by the following detailed results.

1.2.1 Content

The theoretical load of 5F7 was 7.1% w/w. The OD measurements indicated an actual load of 4.7% (Table 3).

This result indicates that, using standard process parameters for fluidized bed granulation satisfactory load of the granules with active agent (Nanobody) can be achieved.

TABLE 3

Quantification results for granulate at t = 0 and after 3 months of storage at 4° C.

| Time point | Average conc (mg/ml, n = 3) | 5F7 load in granulate (w/w) |
|---|---|---|
| T = 0 | 7.25 ± 0.07 | 4.7% |
| T = 3 months | 6.70 ± 0.01 | 4.5% |

After 3 months storage at 4° C. of the 5F7/mannitol granulated sample, still about 96% of the initial content was measured (Table 3).

This result indicates that a granulate comprising Nanobody snows satisfactory storage stability over several months, e.g. 3 months, at a suitable storage temperature, e.g. 4° C.

1.21 SEC Data

SEC chromatograms of the 5F7 reference and the 5F7 granulated material were analyzed, comparing the characteristic peaks as indicated in Table 4 of reference Nanobody kept in solution and the granulated Nanobody. SEC data showed a small increase from 0.1 to 0.7% of the second pre peak after granulation (t=0, Table 4).

TABLE 4

SEC results for granulate at t = 0 and after 3 months of storage at 4° C., compared to reference Nanobody at t = 0

| | % area 5F7 Ref batch | % area granulate t = 0 | % area granulate t = 3 m |
|---|---|---|---|
| Pre-peak 1 | 0.1 | 0.1 | 0.2 |
| Pre-peak 2 | 0.1 | 0.7 | 1.2 |
| Pre-peak 3 | 0.2 | 0.2 | 0.2 |
| Main peak | 99.7 | 99.0 | 98.4 |

After 3 months storage at 4° C. of the 5F7/mannitol granulated sample, SEC data showed a further increase of % pre-peak up to 1.6% (Table 4).

These data provide evidence that the granulation process does not negatively influence the physical integrity of Nanobodies, in particular as regards the formation of agglomerates or any other forms of high molecular weight derivatives.

1.2.3 RPC Data

The 5F7 reference solution and 5F7 granulated material showed comparable RPC chromatograms at the reference time point t=0. Moreover, after 3 months of storage at 4° C., no significant changes were observed on RPC compared to the reference at t=0.

These data provide evidence that Nanobodies are not negatively affected in terms of chemical stability by the granulation process. In particular, the RPC data allow the conclusion that there is no increased occurrence of chemically modified Nanobody species as compared to a reference solution.

1.2.4 Functionality Data

An 80% (4 nM) and 120% (6 nM) test sample were prepared with the reference 5F7 material. Functionality was determined and compared to the 100% 5F7 sample (5 nM). As shown in Table 5, the calculated activities were 75.9% and 116.2% respectively.

TABLE 5

QC of the functionality assay (reference preparations)

| Sample | Average slope (RU/s) (n = 3) | % activity compared to ref |
|---|---|---|
| 5 nM 5F7 Ref | 1.89 | 100.0 |
| 4 nM 5F7 Ref | 1.44 | 75.9 |
| 6 nM 5F7 Ref | 2.20 | 116.2 |
| 5 nM 5F7 ref | 1.89 | 99.6 |

The 5 nM 5F7 solution reference that was injected in the beginning of the experiment was re-analyzed at the end of the experiment and 99.6% functionality was observed (Table 5), indicating that the chip remained stable during the experiment.

TABLE 6

Functional 5F7 concentration in the granulate at t = 0 and after 3 months storage at 4° C.

| Sample | Average slope (RU/s) (n = 3) | % activity compared to ref |
|---|---|---|
| 5 nM 5F7 granulate t = 0 | 1.82 | 96.0 |
| 5 nM 5F7 granulate t = 3 months | 1.59 | 90.9 |

The functionality results of the granulate samples are shown in Table 6, calculated against the reference preparation (Nanobody solution, no granulation).

The activity of the 5F7/mannitol granulated sample (96%) was comparable to the reference sample. No significant changes in functionality were detected after wet granulation and after storage of granulate for 3 months at 4° C.

These data provide evidence that Nanobodies can be granulated in a standard fluidized bed process without suffering any significant loss of function.

1.2.5 Granulate Characterization

Water content and density results are reported in Table 7.

TABLE 7

Water content and densities of granulated 5F7

| Water content (% w/w) | 0.69 |
|---|---|
| Bulk density (g/ml) | 0.67 |
| Tapped density (500 taps) (g/ml) | 0.72 |

Density of the granulate was comparable to the density of the starting material that was used as a carrier (Pearlitol, 0.70-0.76 g/ml).

2 Example 2

Fluid Bed Granulation Making Use of Different Carriers and Binders

Because of the unexpected positive results of the first granulation experiment, the granulation experiment was expanded using two different carriers: mannitol (MAN) (Pearlitol 300 DC; Roquette, Lestrern, France) and lactose (LAC) (SuperTab 11SD; MV-Fonterra).

The granulation experiment was further expanded using two different binders: polyvinylpyrrolidone (PVP) (Kollidon K30, BASF) and hydroxypropylcellulose (HPC) (Klucel EF Pharm, Ashland Aqualon).

2.1 Materials and Methods 2.1.1 Immunoglobulin Single Variable Domain

The Nanobody used in Example 1 was again selected for formulation development by granulation.

2.1.2 Wet Granulation Process

A solution of Nanobody at a concentration of 29.3 mg/ml in water was used as granulation liquid. For the preparation of the binder solution, the Nanobody solution was added to a glass beaker. The binder was added while stirring using a magnetic stirrer until completely dissolved. A binder concentration of 2.2% w/w was applied for concepts with HPC and of 6.2% w/w for concepts with PVP. Qualitative and quantitative composition of the granule concepts is given in Table 15. A Nanobody load of 8.0% was applied.

TABLE 15

Composition of granule concepts

| | Concept | | | | | | | |
|---|---|---|---|---|---|---|---|---|
| | LAC/HPC | | LAC/PVP | | MAN/HPC | | MAN/PVP | |
| Units | g | % | g | % | g | % | g | % |
| Mannitol | — | — | — | — | 50.04 | 85.5 | 50.01 | 72.4 |
| Lactose | 49.98 | 85.5 | 50.01 | 72.4 | — | — | — | — |
| PVP | — | — | 13.50 | 19.60 | — | — | 13.51 | 19.6 |
| HPC | 3.81 | 6.5 | — | — | 3.80 | 6.5 | — | — |
| Nanobody | 4.69 | 8.0 | 5.53 | 8.0 | 4.68 | 8.0 | 5.52 | 8.0 |

This solution was sprayed on the carrier powder (mannitol or lactose) in a fluid bed granulation process. A Mycrolab (Hüttlin GmbH, Schopfheim, Germany) with a 3.8 L insert and with bottom spray configuration was used. The solution was fed to a two-fluid nozzle (diameter: 0.6 mm) by means of a peristaltic pump, type 323 (Watson Marlow, Cornwall, UK).

Process parameters are listed in Table 16. The spray rate was slightly increased during the process. After granulation, the pump and the air heater were switched off and the granules were dried for a short time.

TABLE 16

Process conditions fluid-bed granulation

| Process parameter | LAC/HPC | LAC/PVP | MAN/HPC | MAN/PVP |
|---|---|---|---|---|
| Inlet air volume (m3/h) | 13 | 13 | 17 | 17 |
| Inlet air temperature (° C.) | 59-60 | 56-60 | 54-56 | 55 |
| Product temperature (° C.) | 36-47 | 35-47 | 36-45 | 37-44 |
| Spray rate (ml/mm) | 2.4 | 2.5 | 2.4 | 2.5 |
| Spray air pressure (bar) | 0.4 | 0.4 | 0.4 | 0.4 |
| Microclimate pressure (bar) | 0.5 | 0.5 | 0.5 | 0.5 |
| Spraying time (min) | 75 | 91 | 74 | 90 |
| Product filter blow-out pressure (bar) | 0.8 | 0.8 | 0.8 | 0.8 |
| Product filter blow-out interval (sec) | 9 | 9 | 9 | 9 |

After the process, the powder was cooled down to room temperature and transferred to amber glass vials. The process yield was calculated as the amount of powder collected in the reservoir divided by the theoretical amount of dry material dosed per preparation. The vials were stored at 5° C. After granulation the powder was post-dried in a vacuum oven to remove residual moisture.

2.1.3 Analytical Methods

Sample Preparation and Content Measurement

Sample preparation and content measurements were carried out as described in Example 1. For the determination of the protein concentration, also absorbance at 500 nm (A500) was determined. High absorbance at 500 nm is an indication for the formation of high molecular weight variants.

Purity Assay (Physical Integrity) of the Nanobodies by Size Exclusion High Performance Liquid Chromatography (SE-HPLC)

SE-HPLC was performed on an H-Class Bio (Waters) with DAD-detector. Samples were diluted to 1 mg/ml in MilliQ water before injection on the RPC column.

Samples of the feed solution, of the granules before post-drying and of the granules after post-drying were analyzed. The relative amount of protein purity was expressed as area %, and was calculated by dividing the peak area by the total (main peak+impurities) integrated area.

Purity Assay (Chemical Integrity) and Quantification of the Nanobodies by Reversed Phase High Performance Liquid Chromatography (RP-HPLC, or RPC)

RP-HPLC was performed on an H-Class (Waters) with TUV-detector. Samples were diluted to 1 mg/ml in MilliQ water before injection on the RPC column.

Samples of the feed solution, of the granules before post-drying and of the granules after post-drying were analyzed. The relative amount of protein purity was expressed as area %, and was calculated by dividing the peak area by the total (main peak+impurities) integrated area.

2.2 Results

2.2.1 Yield and Content

A free flowing powder was obtained for all concepts. Results of process yield and water content before and after the post-drying process are listed in Table 17. As listed in Table 17, the process yield was 88% w/w or higher.

After granulation, concepts with PVP as a binder had a higher water content compared to concepts with HPC. This difference was undone by post-drying of the powder in a successive vacuum drying process. The water content of concepts with mannitol was lower (<1%) than concepts with lactose (5%).

TABLE 17

Process yields and water content of different lots of granules

| Concept | LAC/HPC | LAC/PVP | MAN/HPC | MAN/PVP |
|---|---|---|---|---|
| Process yield (% w/w) | 88 | 92 | 93 | 94 |
| Water content (% w/w) BD* | 3.27 | 5.13 | 0.82 | 2.57 |
| Water content (% w/w) AD* | 4.76 | 4.73 | 0.56 | 0.68 |

*BD: before post-drying; AD: after post-drying

2.2.2 SEC Data

In order to evaluate the effect of the granulation process on the purity of 5F7, SEC analysis was performed on the feed solution, the granules before post-drying and the granules after post-drying. Pure Nanobody 5F7 was monitored in parallel. The results are shown in Table 18.

TABLE 18

SEC results of granulation of Nanobody 5F7 with mannitol or lactose as carrier and HPC or PVP as binder

| | Nanobody 5F7 | | | | | |
|---|---|---|---|---|---|---|
| | Average area % main peak | | | Average area % pre peak | | |
| | Feed | Gran BD* | Gran AD* | Feed | Gran BD* | Gran AD* |
| Ref solution | | 99.90 | | | 0.10 | |
| Lactose/PVP | 99.94 | 99.50 | 99.52 | 0.06 | 0.50 | 0.49 |
| Mannitol/HPC | ND | 98.66 | 98.51 | HD | 1.32 | 1.49 |
| Lactose/HPC | 99.91 | 99.98 | 99.52 | 0.09 | 1.02 | 0.48 |
| Mannitol/PVP | 99.94 | 99.23 | 99.32 | 0.06 | 0.74 | 0.68 |

*Gran BD: granulate before drying; Gran AD: granulate after drying

The SEC results showed little influence of the granulation process on aggregation. There was a slight increase in pre-peak formation (RRT0.91).

The peak pattern was stable at storage, and did not differ significantly even after e.g. 3 months storage at 4° C.

2.2.3 RPC Data

In order to evaluate the effect of the granulation process on the purity of 5F7, RPC analysis was performed on the feed solution, the granules before post-drying and the granules after post-drying. Pure Nanobody 5F7 was monitored in parallel. The results are shown in Table 19.

TABLE 19

RPC results of granulation of Nanobody 5F7 with mannitol and lactose as carrier and HPC and PVP as binder

| | Nanobody 5F7 | | | | | | | | |
|---|---|---|---|---|---|---|---|---|---|
| | Average area % main peak | | | Average area % post peak | | | Average area % pre peak | | |
| | Feed | Gran BD* | Gran AD* | Feed | Gran BD* | Gran AD* | Feed | Gran BD* | Gran AD* |
| Ref solution | | 95.17 | | | 4.82 | | | 0 | |
| Lactose/PVP | 94.81 | 93.53 | 92.43 | 4.34 | 4.82 | 5.70 | 0.84 | 1.65 | 1.87 |
| Mannitol/HPC | ND | 94.76 | 94.30 | ND | 4.34 | 4.70 | ND | 0.9 | 0.98 |
| Lactose/HPC | 95.23 | 94.42 | 94.10 | 4.27 | 4.56 | 4.90 | 0.50 | 1.02 | 0.90 |
| Mannitol/PVP | 94.93 | 94.73 | 92.60 | 4.34 | 4.28 | 5.50 | 0.73 | 0.99 | 1.90 |

*Gran BD: granulate before drying; Gran AD: granulate after drying

Concepts with HPC as binder showed an increase in total pre- and post-peak area % of not more than 1% throughout the process. Concepts using PVP as a binder showed an increase of one of the post-peaks (RRT1.09) upon post-drying. For these concepts an increase in total pre- and post-peak area % of about 2.5% was detected throughout the process.

The peak pattern was stable at storage, and did not differ significantly even after e.g. 3 months storage at 4° C.

2.2.4 UV Measurement

UV measurement was carried out on the feed solution, the granules before post-drying and the granules after post-drying. No turbidity was observed in any of the samples. The carrier or binder used did not impact Nanobody contents.

3 Example 3

Fluid Bed Granulation of Different Nanobodies

Because of the unexpected positive results of the first granulation experiment, the granulation experiment was expanded using three different Nanobodies. Based on the results in Example 2, mannitol was selected as carrier and HPC as binder.

3.1 Materials and Methods 3.1.1 Immunoglobulin Single Variable Domain

A monovalent, bivalent and trivalent Nanobody was evaluated in this study. The Nanobodies had the following sequence:

| Nanobody | SEQ ID NO | Sequence |
|---|---|---|
| 5F7 | 1 | EVQLVESGGGLVQAGGSLRLSCAASGITFSINTMGWYRQAPGKQRELVALISSIG DTYYADSVKGRFTISRDNAKNTVYLQMNSLKPEDTAVYYCKRFRTAAQGTDYWG QGTQVTVSS |
| NB2 | 2 | DVQLVESGGGLVQPGGSLRLSCAASGRTFSYNPMGWFRWAPGKGRELVAAISRT GGSTYYPESVEGRFTISRDNAKRTVYLQMNSLRAEDTAVYYCAAAGVRAEQGRV RTLPSEYTFWGQGTQVTVSSAAAEVQLVESGGGLVQPGGSLRLSCAASGRTFSY NPMGWFRQAPGKGRELVAAISRTGGSTYYPESVEGRFTISRDNAKRTVYLQMNS LRAEDTAVYYCAAAGVRAEQGRVRTLPSEYTFWGQGTQVTVSS |
| NB3 | 3 | EVQLVESGGGLVQAGGSLSISCAASGGSLSNYVLGWFRQAPGKEREFVAAINWR GDITIGPPNVEGRPTISRDNAKNTGYLQMNSLAPDDTAVYYCGAGTPLNPGAYIY DWSYDYWGRGTQVTVSSGGGGSGGGGSGGGGSEVQLVESGGGLVQAGGSLSI SCAASGGSLSNYVLGWFRQAPGKEREFVAAINWRGDITIGPPNVEGRFTISRDNA KNTGYLQMNSLAPDDTAVYYCGAGTPLNPGAYIYDWSYDYWGRGTQVTVSSG GGGSGGGGSGGGGSEVQLVESGGGLVQAGGSLSISCAASGGSLSNYVLGWFRQ APGKEREFVAAINWRGDITIGPPNVEGRFTISRDNAKNTGYLQMNSLAPDDTAV YYCGAGTPLNPGAYIYDWSYDYWGRGTQVTVSS |

3.1.2 Wet Granulation Process

A solution of Nanobody at a concentration of 29.3 mg/ml (5F7), 32.88 mg/ml (NB2) and 51.27 mg/ml (NB3) in water was used as granulation liquid. For the preparation of the binder solution, the Nanobody solution was added to a glass beaker. The binder (HPC) was added while stirring using a magnetic stirrer until completely dissolved. A binder concentration of 2.2% w/w was applied. Qualitative and quantitative composition of the granule concepts is given in Table 20. A Nanobody load of 8.0% w/w with 5F7, 9.5% w/w with NB2 and of 14.1% w/w with NB3 was applied.

TABLE 20

Composition of granule concepts

| | Concept | | | | | |
|---|---|---|---|---|---|---|
| | 5F7 | | NB2 | | NB3 | |
| Units | g | % | g | % | g | % |
| Mannitol | 50.04 | 85.5 | 50.01 | 84.1 | 50.00 | 79.8 |
| HPC | 3.80 | 6.5 | 3.80 | 6.4 | 3.80 | 6.1 |
| Nanobody | 4.68 | 8.0 | 5.67 | 9.5 | 8.83 | 14.1 |

This solution was sprayed on the carrier powder (mannitol) in a fluid bed granulation process. A Mycrolab (Hüttlin GmbH, Schopfheim, Germany) with a 3.8 L insert and with bottom spray configuration was used. The solution was fed to a two-fluid nozzle (diameter: 0.6 mm) by means of a peristaltic pump, type 323 (Watson Marlow, Cornwall, UK).

Process parameters are listed in Table 21. The spray rate was slightly increased during the process. After granulation, the pump and the air heater were switched off and the granules were dried for a short time.

TABLE 21

Process conditions fluid-bed granulation

| Process parameter | 5F7 | NB2 | NB3 |
|---|---|---|---|
| Inlet air volume (m3/h) | 17 | 17 | 17 |
| Inlet air temperature (° C.) | 54-56 | 54-55 | 54 |
| Product temperature (° C.) | 36-45 | 36-44 | 36-44 |
| Spray rate (ml/min) | 2.4 | 2.4 | 2.5 |
| Spray air pressure (bar) | 0.4 | 0.4 | 0.4 |
| Microclimate pressure (bar) | 0.5 | 0.5 | 0.5 |
| Spraying time (min) | 74 | 73 | 74 |
| Product filter blow-out pressure (bar) | 0.8 | 0.8 | 0.8 |
| Product filter blow-out interval (sec) | 9 | 9 | 9 |

After the process, the powder was cooled down to room temperature and transferred to amber glass vials. The process yield was calculated as the amount of powder collected in the reservoir divided by the theoretical amount of dry material dosed per preparation. The vials were stored at 5° C. After granulation the powder was post-dried in a vacuum oven to remove residual moisture.

3.13 Analytical Methods

Sample Preparation and Content Measurement

Sample preparation and content measurements were carried out as described in Example 1. For the determination of the protein concentration, also absorbance at 500 nm (A500) was determined. High absorbance at 500 nm is an indication for the formation of high molecular weight variants.

Purity Assay (Physical Integrity) of the Nanobodies by Size Exclusion High Performance Liquid Chromatography (SE-HPLC)

SE-HPLC was performed on an H-Class Bio (Waters) with DAD-detector. For Nanobody 5F7 and NB2, samples were diluted to 1 mg/ml in MilliQ water before injection on the RPC column. For NB3, samples were diluted to 2 mg/ml in MilliQ water and further used 1:1 (vol) with MilliQ water.

Samples of the feed solution, of the granules before post-drying and of the granules after post-drying were analyzed. The relative amount of protein purity was expressed as area %, and was calculated by dividing the peak area by the total (main peak+impurities) integrated area.

Purity Assay (Chemical Integrity) and Quantification of the Nanobodies by Reversed Phase High Performance Liquid Chromatography (RP-HPLC, or RPC)

For Nanobody 5F7 and NB3, RP-HPLC was performed on an H-Class (Waters) with TUV-detector. For N82, RP-HPLC was performed on both a H-Class (Waters) with TUV-detector and a H-Class bio (Waters) with DAD-detector. For Nanobody 5F7 and N82, samples were diluted to 1 mg/ml in MilliQ water before injection on the RPC column. For NB3, samples were diluted to 2 mg/ml in MilliQ water and further used 1:1 (vol) with 36% isopropanol.

Samples of the feed solution, of the granules before post-drying and of the granules after post-drying were analyzed. The relative amount of protein purity was expressed as area %, and was calculated by dividing the peak area by the total (main peak+impurities) integrated area.

3.2 Results 3.2.1 Yield and Content

A free flowing powder was obtained for all concepts. Results of process yield and water content before and after the post-drying process are listed in Table 22.

As listed in Table 22, the process yield was 92% w/w or higher.

TABLE 22

Process yields and water content of different lots of granules

| Concept | 5F7 | NB2 | NB3 |
|---|---|---|---|
| Process yield (% w/w) | 93 | 92 | 97 |
| Water content (% w/w) BD* | 0.82 | 1.07 | 1.40 |
| Water content (% w/w) AD* | 0.56 | 0.60 | 0.54 |

*BD: before post-drying; AD: after post-drying 3.2.2 SEC Data

In order to evaluate the effect of the granulation process on the purity of the tested Nanobodies, SEC analysis was performed on the feed solution, the granules before post-drying and the granules after post-drying. Pure Nanobody was monitored in parallel. The results are shown in Table 23

TABLE 23

SEC results of granulation of Nanobody 5F7, NB2 and NB3

| | Average area % main peak | | | Average area % pre peak | | |
|---|---|---|---|---|---|---|
| | Feed | Gran BD* | Gran AD* | Feed | Gran BD* | Gran AD* |
| Ref solution 5F7 | | 99.90 | | | 0.10 | |
| 5F7 | ND | 98.66 | 98.51 | ND | 1.32 | 1.49 |
| Ref solution NB2 | | 99.87 | | | 0.13 | |
| NB2 | 100 | 98.96 | 98.83 | 0.00 | 1.04 | 1.17 |
| Ref solution NB3 | | 99.75 | | | 0.25 | |
| NB3: 15% load | 99.79 | 98.80 | 98.61 | 0.21 | 1.20 | 1.39 |
| NB3: 8% load | ND | ND | 98.98 | ND | ND | 1.06 |

*Gran BD: granulate before drying; Gran AD: granulate after drying

The SEC results show little influence of the granulation process on aggregation of NB2. There was a slight increase in pre-peak formation (RRT0.91). For NB3, a pre-peak at RRT0.87 increases from 0.25 to about 1.10 area %.

The peak pattern was stable at storage, and did not differ significantly even after e.g. 3 months storage at 4° C.

3.2.3 RPC Data

In order to evaluate the effect of the granulation process on the purity of the tested Nanbodies, RPC analysis was performed on the feed solution, the granules before post-drying and the granules after post-drying. Pure Nanobody was monitored in parallel. The results are shown in Table 24.

TABLE 24

RPC results of granulation of Nanobody 5F7, NB2 and NB3

| | Average area % main peak | | | Average area % post peak | | | Average area % pre peak | | |
|---|---|---|---|---|---|---|---|---|---|
| | Feed | Gran BD* | Gran AD* | Feed | Gran BD* | Gran AD | Feed | Gran BD* | Gran AD* |
| Ref solution | | 95.17 | | | 4.82 | | | 0 | |
| 5F7 | ND | 94.76 | 94.30 | ND | 4.34 | 4.70 | ND | 0.9 | 0.98 |
| Ref solution NB2 | | 85.24 | | | 12.29 | | | 2.45 | |
| NB2 | 86.22 | 84.60 | 84.0 | 11.34 | 12.57 | 13.00 | 2.45 | 2.82 | 3.01 |
| Ref solution NB3 | | 95.16 | | | 3.67 | | | 1.18 | |
| NB3: 15% load | 95.16 | 88.53 | 90.62 | 3.66 | 9.86 | 7.99 | 1.18 | 1.62 | 1.38 |
| NB3: 8% load | ND | ND | 95.71 | ND | ND | 3.33 | ND | ND | 0.96 |

*Gran BD: granulate before drying; Gran AD: granulate after drying

The RPC results showed no significant influence of the granulation process on the purity of the NB2. RPC results showed an influence of the duration of the granulation process on degradation of NB3. The pre- and/or post-peak formation was not increased for an 8% granule sample taken during the granulation process, while for samples taken after the entire process cycle (14% load), post-peak levels increased with 2.5% for RRT1.07 (pyroglutamate) and 1% for RRT1.11, and a new post-peak of about 3 area % forms at RRT1.20.

The peak pattern was stable at storage, and did not differ significantly even after e.g. 3 months storage at 4° C.

3.2.4 LTV Measurement

UV measurement was carried out on the feed solution, the granules before post-drying and the granules after post-drying. The granulation process did not impact Nanobody contents.

4 Example 2

Bead Coating 4.1 Materials and Methods
4.1.1 Immunoglobulin Single Variable Domain The same immunoglobulin single variable domain as in example 1 was used.

4.1.2 Bead Coating Process

Capsules filled with coated beads with a total dose of 30 mg of Nanobody were developed.

For the preparation of Nanobody coated beads, a bottom-spray fluid bed coating process was applied. A Mycrolab (Hüttlin GmbH, Schopfheirh, Germany) with a 3.8 L insert was used.

The coating solution was fed to a two-fluid nozzle (diameter; 0.6 mm) by means of a peristaltic pump, type 323 (Watson Marlow, Cornwall, UK), Inert microcrystalline cellulose (MCC) spheres with a particle size of 700-1000 μm were used as a carrier. Initial batch size was approximately 60 g. The coating solution was prepared as follows. Demineralized water was filled in a glass beaker. The Nanobody solution was added. Specifically, a solution of Nanobody 5F7 in water at a concentration of 29.3 mg/ml was used. Hydroxypropylmethylcellulose 5 mPa·s (HPMC E5), a film forming polymer, was added while stirring with a magnetic stirrer until dissolved. The theoretical solids concentration of the spraying solution was 6.4% (w/w). The composition of the coating is shown in Table 8.

TABLE 8

Composition of the coating solution for the preparation of Nanobody loaded beads

| Material | Quantity (g/batch) |
|---|---|
| Nanobody 5F7 solution | 138.606 |
| HPMC E5 | 6.401 |
| Demineralised water | 15.028 |

The spray rate was slightly increased during the process. After coating the pump and the air heater were switched off and beads were dried for a short time (approx. min.). After the process the beads were cooled to room temperature and transferred to an amber glass vial. The vial was stored at 5° C. The process yield was calculated as the amount of beads collected in the reservoir divided by the theoretical amount of solids used in the formulation. Process parameters are listed in Table 9. The composition of the beads is shown in Table 10.

TABLE 8

Conditions fluid bed coating process

| Process parameter | Target value |
|---|---|
| Inlet air volume (m3/h) | 17 |
| Inlet air temperature (° C.) | 70 |
| Outlet air temperature (° C.) | 39-46 |
| Product temperature (° C.) | 46-56 |
| Spray rate (g/min) | 2.2-2.8 |
| Spray air pressure (bar) | 0.8 |
| Microclimate air pressure (bar) | 0.3 |
| Coating time (min) | 59 |
| Drying time (min) | 7 |

TABLE 9

Composition of the beads

| Material | Quantity (g/batch) | Quantity (mg/capsule) |
|---|---|---|
| Nanobody solution (solid) | 3.841 | 30.00 |
| Water Nanobody solution* | 134.765 | |
| HPMC E5 | 6.401 | 50.00 |
| Demineralised water* | 15.028 | 117.38 |
| Microcrystaliine cellulose (MCC) spheres (Cellets 700) | 47.370 | 370.00 |

*does not appear in the final product

The coated beads were filled in a size 0 hard gelatin capsule at a dose of 30 mg Nanobody.

4.13 Analytical Methods and Characterisation

The coated beads were analyzed using the same methods as described in the context of example 1.

Sample preparation was performed as follows: 200 mg of 5F7 coated MCC spheres were weighed and put in a 50 ml falcon tube with 3 ml of D-PBS. They were extracted in a rotating shaker for at least 4 hours. A sample of supernatant was taken, put in a 1.5 ml Eppendorf tube and centrifuged at high speed (20000 g).

4.2 Results and Discussion

Fluid bed coating of inert beads resulted in spherical particles with a narrow size distribution and a Nanobody load of 7.1%. An acceptable loss of functionality was detected.

4.2.1 Content

TABLE 10

OD results for Nanobody loaded beads (n = 3)

| Average conc (mg/ml) | 5F7 load in beads |
|---|---|
| 4.76 | 7.1% |

The theoretical load of 5F7 for the beads was 6.4%; OD measurements indicated an actual 5F7 load of 7.1% (Table 11).

This result demonstrates that Nanobodies can be successfully coated in a standard coating process and satisfactory Nanobody loads can be achieved.

4.2.2 SEC Data

SE-HPLC analysis showed an increase of pre-peaks compared to reference (total pre peaks from 0.41 to 2.63%) (Table 12). The presence of HPMC did not interfere with the measurements (Table 12).

This result indicates only a slight (and acceptable) increase in higher molecular weight species, and confirms that the coating process did not lead to any significant formation of higher molecular weight species of Nanobodies.

TABLE 11

SEC results for HPMC + 5F7 solution, 5F7 coated beads compared to 5F7 reference

|  | % area 5F7 Ref batch | % area HMPC + 5F7 | % area 5F7 coated beads |
| --- | --- | --- | --- |
| Pre-peak 1 | 0.00 | 0.1 | 0.1 |
| Pre-peak 2 | 0.09 | 0.2 | 0.8 |
| Pre-peak 3 | 0.09 | 0.2 | 1.5 |
| Pre-peak 4 | 0.23 | 0.3 | 0.2 |
| Main peak | 99.58 | 99.2 | 97.4 |

4.2.3 RPC Data

No significant increase of the pre-peaks and post-peaks was detected on RPC as compared to a reference preparation (Nanobody starting solution).

This result indicates that there was no formation of chemically modified derivatives of the Nanobody caused by the coating process.

4.2.4 Functionality Data

After bead coating with 5F7 solution a minor loss of functionality was detected (Table 13).

TABLE 12

Functionality data of 5F7 coated beads via Biacore

| Sample | Average slope (RU/s) (n = 3) | % activity compared to ref |
| --- | --- | --- |
| 5 nM 5F7 Ref | 2.03 | 100.0 |
| 5 nM 5F7 coated beads | 1.55 | 76.5 |

These results indicate that Nanobodies can be applied to inert carriers in a standard coating process and will retain acceptable levels of activity.

4.2.5 Characteristics of Coated Beads

TABLE 13

Water content of 5F7 coated beads via LOD measurement

| | |
|---|---|
| Water content (% w/w) (LOD) | 2.63 |

The invention claimed is:

1. Method of producing a solid formulation of an immunoglobulin single variable domain, wherein a solid carrier material is agitated and contacted with a liquid comprising an immunoglobulin single variable domain as an active agent and concomitantly heat is applied to evaporate the liquid, wherein the method is a wet granulation or a coating process, and wherein the use of a protein matrix with a salt concentration between 63.7 and 85.3% based on dry solids is excluded.

2. The method according to claim 1, which is a wet granulation process, such as a fluid bed granulation process.

3. The method according to claim 1, wherein the solid carrier material is one or more selected from disaccharides like lactose, maltitol, sucrose, maltose; polyols or sugar alcohols like mannitol, sorbitol, isomalt; calcium phosphate; polysaccharides such as maltodextrin, starch and starch derivatives, pregelatinised starch, inulin; cellulose; or mixtures thereof.

4. The method according to claim 1, wherein in addition a binder is used, such as one or more selected from starch, starch paste, partially pregelatinised starch, gelatine and cellulose derivatives such as hydroxypropylmethyl cellulose, hydroxyethyl cellulose, hydroxypropyl cellulose, polyvinyl pyrrolidone, copovidone, polydextrose, carbomer or mixtures thereof.

5. The method according to claim 1, which is a coating process, in particular a fluid bed coating process.

6. The method according to claim 5, wherein the solid carrier is selected from powders and beads, in particular inert nonpareil beads, more in particular beads selected from one or more of microcrystalline cellulose, sucrose, or mixtures thereof.

7. The method according to claim 1, wherein the immunoglobulin single variable domain comprises one or more selected from a VHH immunoglobulin single variable domain, a humanized VHH immunoglobulin single variable domain or a camelized VH immunoglobulin single variable domain or any suitable fragment or combination thereof.

8. The method according to claim 1, wherein the immunoglobulin single variable domain is a monovalent or a bivalent construct.

9. The method according to claim 1, wherein the residual liquid content of the solid formulation is less than 10% (w/w), preferably less than 5%, less than 2.5% or less than 1% of the final solid formulation.

10. The method according to claim 1, wherein the solid carrier is agitated by one or more of mixing, stirring, shaking, by applying a gas stream, or by combinations thereof.

11. The method according to claim 1, wherein heat is applied in the form of a heated gas stream, preferably a heated air stream, which is directed at the solid carrier material such that a fluid bed is formed.

12. The method according to claim 1, wherein the temperature of the solid carrier material contacted with a liquid comprising an immunoglobulin single variable domain as an active agent ranges between 40° C. and 80° C., more specifically between 40° C. and 70° C., preferably between 40° C. and 60° C., more preferably between 40° C. and 55° C., wherein each of the values is understood to allow for a variation of ±2° C.

13. The method according to claim 1, wherein the solid carrier material is contacted with the liquid comprising the active agent by spraying, in particular by spraying the liquid onto a fluid bed of the solid carrier material.

14. The method according to claim 1, wherein the solid carrier material is agitated and contacted with a liquid comprising an immunoglobulin single variable domain and concomitantly heat is applied to evaporate the liquid for at least 15 min, for example at least 20 min, at least 30 min, at least 40 min, at least 50 min.

15. The method according to claim 1, wherein the liquid comprising the active agent is selected from water or an aqueous buffer.

16. The method according to claim 15, wherein the liquid further comprises excipients.

17. The method according to claim 1, wherein the liquid comprising the active agent has a salt concentration of less than 15% (w/w), preferably less than 10%, e.g. less than 9%, 8%, 7%, 6% or 5%.

18. The method according to claim 1, which further comprises a step of manufacturing a tablet, capsule or implant.

19. Solid formulation obtainable by a method according to claim 1.

20. Method for preparing a pharmaceutical preparation such as a capsule or a tablet using a solid formulation obtainable by the method according to claim 1.

21. Pharmaceutical preparation obtainable according to the method of claim 20.

* * * * *